(12) United States Patent
Shimizu

(10) Patent No.: US 10,428,005 B2
(45) Date of Patent: Oct. 1, 2019

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 15/542,621

(22) PCT Filed: May 25, 2017

(86) PCT No.: PCT/JP2017/019578
§ 371 (c)(1),
(2) Date: Jul. 10, 2017

(87) PCT Pub. No.: WO2018/173307
PCT Pub. Date: Sep. 27, 2018

(65) Prior Publication Data
US 2018/0273459 A1    Sep. 27, 2018

(30) Foreign Application Priority Data
Mar. 22, 2017    (JP) .................. 2017-056300

(51) Int. Cl.
C07C 51/12 (2006.01)
C07C 51/44 (2006.01)
B01D 3/00 (2006.01)
B01D 3/14 (2006.01)

(52) U.S. Cl.
CPC .............. *C07C 51/12* (2013.01); *B01D 3/009* (2013.01); *B01D 3/143* (2013.01); *C07C 51/44* (2013.01); *C07C 51/445* (2013.01)

(58) Field of Classification Search
None
See application file for complete search history.

(56) References Cited

U.S. PATENT DOCUMENTS

| | | |
|---|---|---|
| 5,371,286 A | 12/1994 | Blay et al. |
| 5,625,095 A | 4/1997 | Miura et al. |
| 5,723,660 A | 3/1998 | Morimoto et al. |
| 5,756,836 A | 5/1998 | Shimizu et al. |
| 6,143,930 A | 11/2000 | Singh et al. |
| 2015/0299084 A1 | 10/2015 | Shimizu et al. |
| 2016/0102036 A1 | 4/2016 | Shaver |
| 2016/0221909 A1 | 8/2016 | Shaver et al. |

FOREIGN PATENT DOCUMENTS

| | | |
|---|---|---|
| EP | 0 497 521 A2 | 8/1992 |
| EP | 0 645 362 A1 | 3/1995 |
| EP | 0 687 662 A2 | 12/1995 |
| EP | 0 768 295 A1 | 4/1997 |
| EP | 2 657 220 A1 | 10/2013 |
| EP | 2 937 329 A1 | 10/2015 |
| JP | 4-295445 A | 10/1992 |
| JP | 7-025813 A | 1/1995 |
| JP | 7-133249 A | 5/1995 |
| JP | 8-020555 A | 1/1996 |
| JP | 2001-508405 A | 6/2001 |
| JP | 2016-164137 A | 9/2016 |
| JP | 2016-539078 A | 12/2016 |
| WO | WO 96/33965 A1 | 10/1996 |
| WO | WO 98/17619 A2 | 4/1998 |
| WO | WO 2014/097867 A1 | 6/2014 |
| WO | WO 2016/054608 A1 | 4/2016 |
| WO | WO 2016/122728 A1 | 8/2016 |

OTHER PUBLICATIONS

English translation of the Written Opinion of the International Searching Authority (Forms PCT/IB/310 and PCT/ISA/237) for International Application No. PCT/JP2017/019578, dated Sep. 14, 2017.
Exended European Search Report dated Mar. 15, 2018, in European Patent Application No. 17739175.2.
International Search Report (PCT/ISA/210) issued in PCT/JP2017/019578, dated Jun. 26, 2017.
Japanese Notification of Reasons for Rejection for Application No. 2017-536045, dated Jul. 10, 2018, with English language translation.

*Primary Examiner* — Ana Z Muresan
(74) *Attorney, Agent, or Firm* — Birch, Stewart, Kolasch & Birch, LLP

(57) ABSTRACT

It is intended to provide a method capable of industrially and efficiently producing acetic acid having a good potassium permanganate test value without a large cost.
The method includes a step of distilling an aqueous phase and/or an organic phase of a column top condensate of a lower boiling point component removal column by a crotonaldehyde removal column; and the reflux ratio of the lower boiling point component removal column is not less than 2 (when the aqueous phase is refluxed), and the crotonaldehyde removal column is operated such that at least one of the following conditions (i) to (iii) is satisfied:
  (i) the reflux ratio of the distillation column is not less than 0.01;
  (ii) the ratio of the crotonaldehyde concentration (ppm by mass) in a distillate liquid of the distillation column to the crotonaldehyde concentration (ppm by mass) in a charging mixture (former/latter) is less than 1; and
  (iii) the ratio of the crotonaldehyde concentration (ppm by mass) in a bottom fraction of the distillation column to the crotonaldehyde concentration (ppm by mass) in a charging mixture (former/latter) is more than 1.

20 Claims, 5 Drawing Sheets

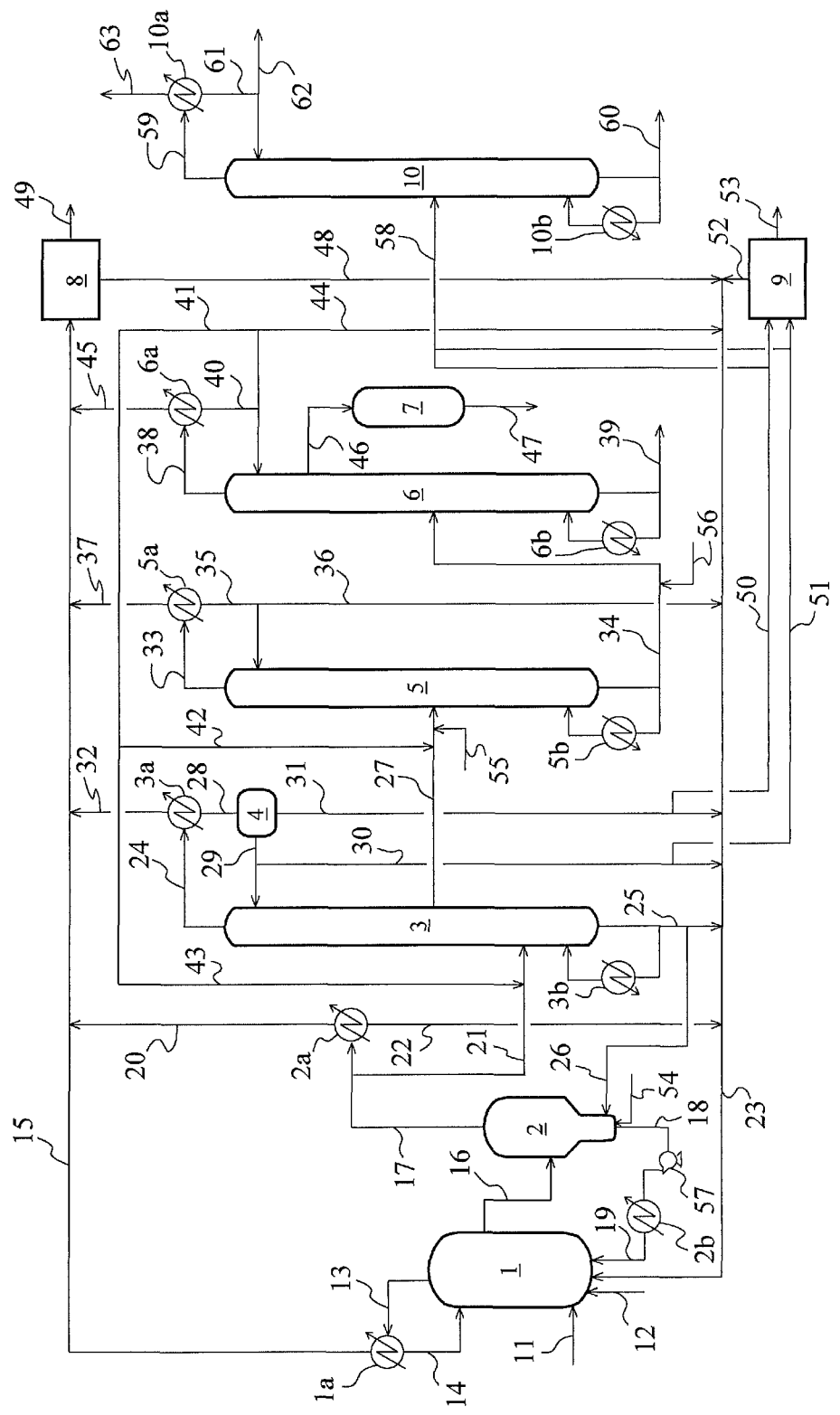
[Figure 1]

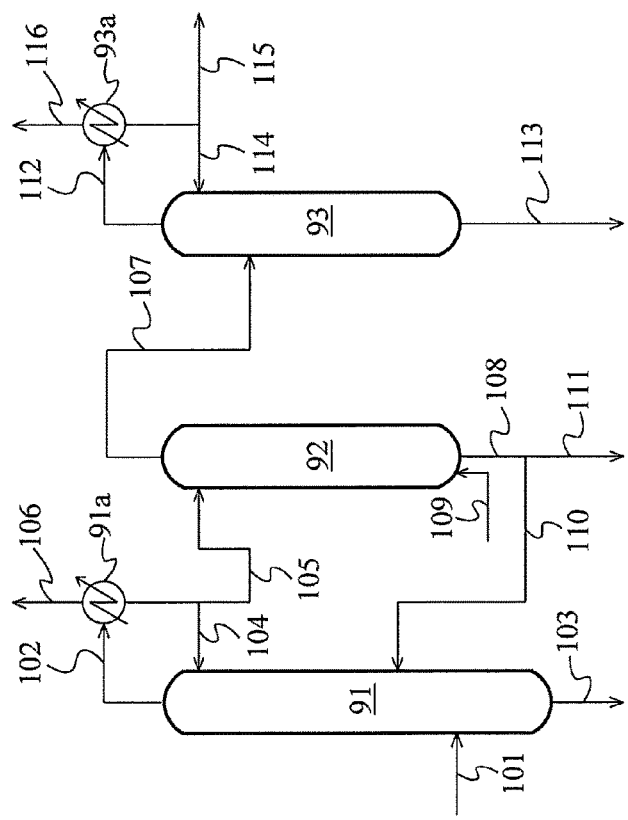
[Figure 2]

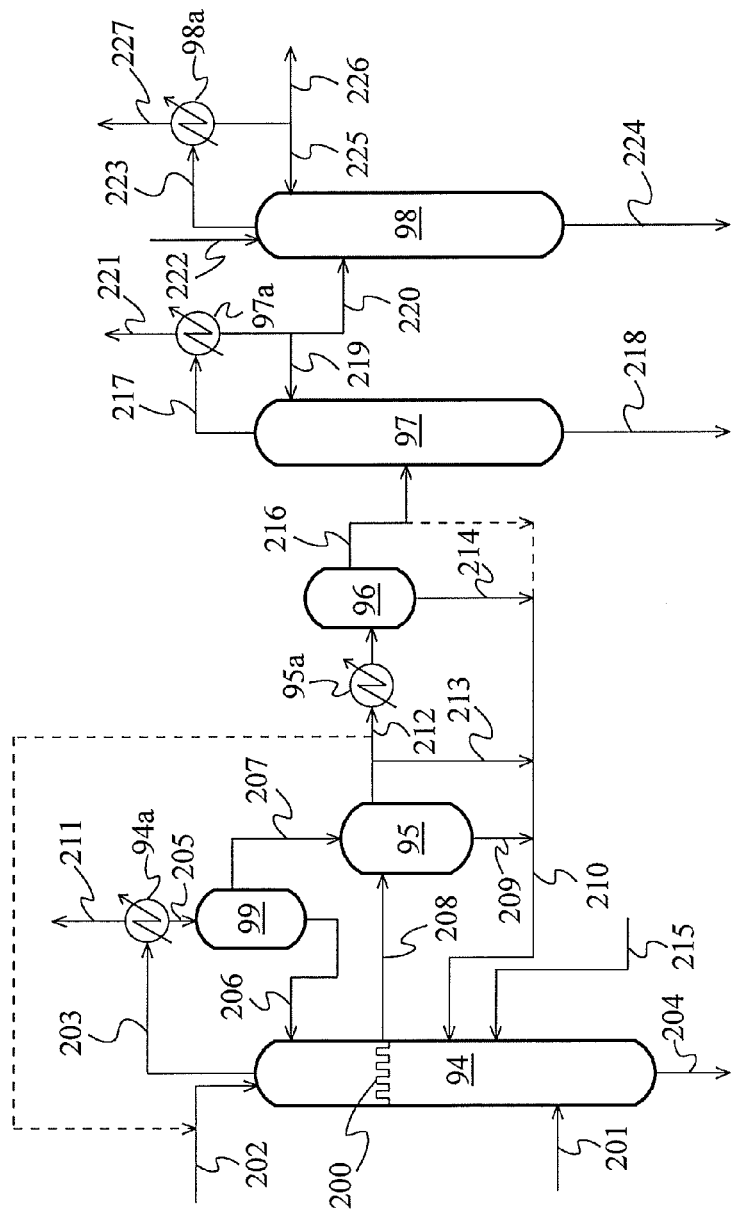
[Figure 3]

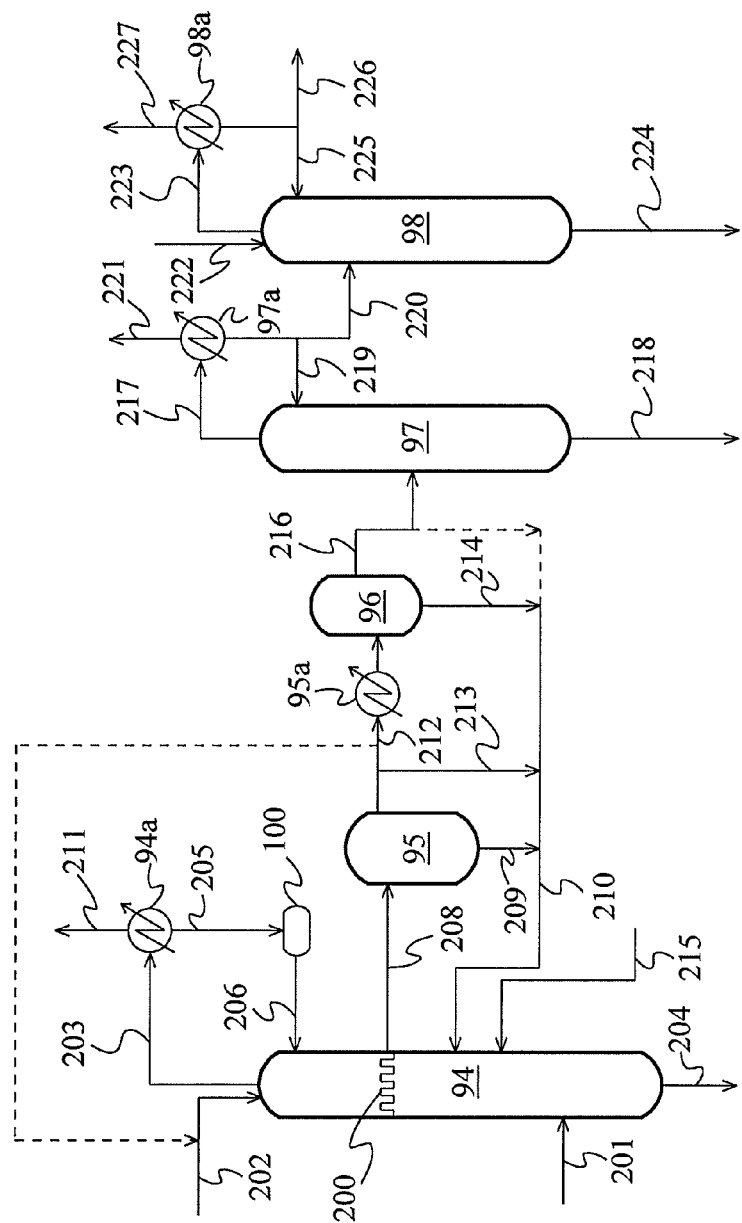
[Figure 4]

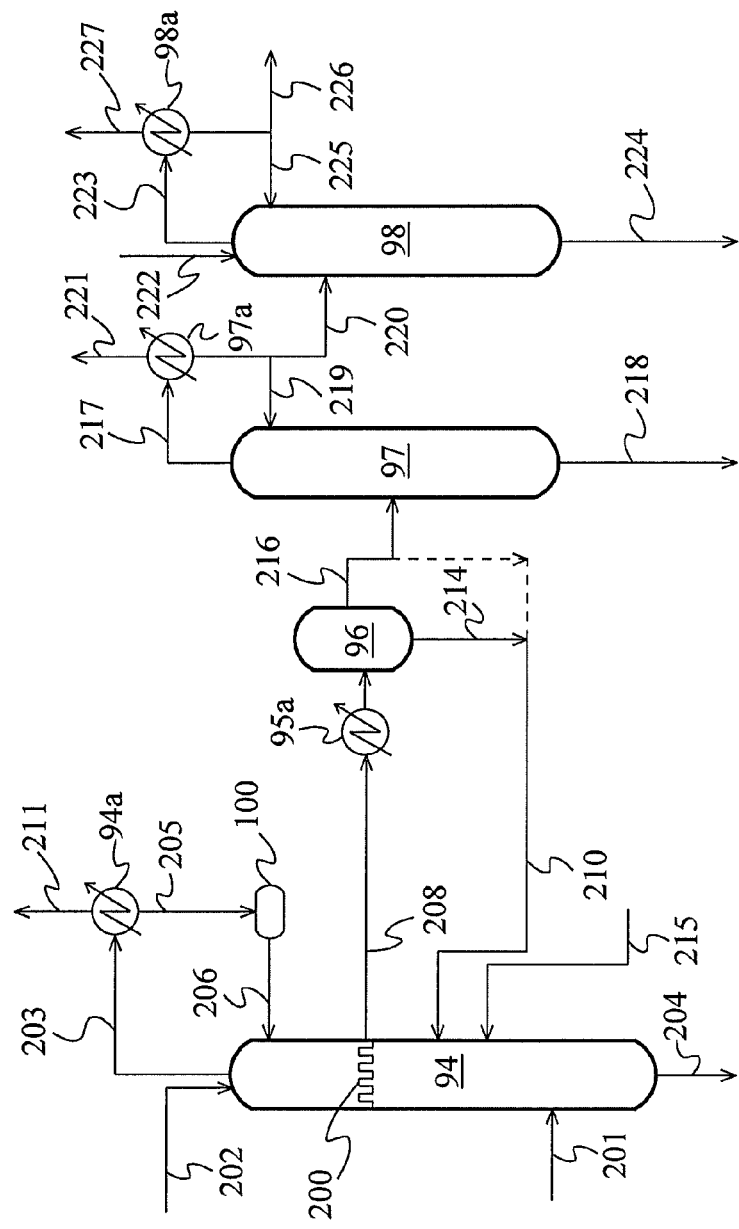
[Figure 5]

METHOD FOR PRODUCING ACETIC ACID

TECHNICAL FIELD

The present invention relates to a method for producing acetic acid. The present application claims the priority of Japanese Patent Application No. 2017-056300 filed in Japan on Mar. 22, 2017, the contents of which are incorporated herein by reference in their entirety.

BACKGROUND ART

A carbonylation process of a methanol method (an acetic acid production process of a methanol method) is known as an industrial method for producing acetic acid. In this process, for example, methanol and carbon monoxide are reacted in the presence of a catalyst in a reaction vessel to produce acetic acid. The reaction mixture is evaporated in an evaporator, and the vapor phase is purified in a lower boiling point component removal column and subsequently in a dehydration column so that product acetic acid is prepared. Alternatively, product acetic acid is prepared via a higher boiling point component removal column subsequent to the dehydration column, and further, a product column.

In such a process for producing acetic acid acetaldehyde formed through reduction of methyl iodide is changed to crotonaldehyde through an aldol condensation to deteriorate a potassium permanganate test value (permanganate time) of the product acetic acid. Further, crotonaldehyde is changed to 2-ethyl crotonaldehyde through an aldol condensation with acetaldehyde, and 2-ethyl crotonaldehyde also deteriorates a potassium permanganate test value of the product acetic acid. However, the degree of deterioration of a potassium permanganate test value per unit mass by crotonaldehyde is severer than the same by 2-ethyl crotonaldehyde, and quality deterioration becomes more significant, when crotonaldehyde is contained in a product acetic acid.

For reducing crotonaldehyde or 2-ethyl crotonaldehyde, there have been heretofore two major groups of industrially applied methods, namely:
(i) a method for suppressing formation of crotonaldehyde in a reaction system by means of separation and removal of acetaldehyde by-produced in a reaction system from methyl iodide in a purification step so as to decrease acetaldehyde in methyl iodide recycled to the reaction system; and
(ii) a method by which crotonaldehyde contained in crude acetic acid obtained in the course of a purification step is directly decomposed by oxidation with ozone (Patent Literatures 1 and 2). However, a separation and removal apparatus for acetaldehyde and an ozonization apparatus are both expensive. Improvement of a potassium permanganate test value of product acetic acid has heretofore relied entirely on the methods, which leads to increase in apparatus costs.

Meanwhile, it has been known that alkanes are formed as impurities in an acetic acid production process of a methanol method. The alkanes have a carbon number of not less than 3 and are impurities with a boiling point higher than that of methyl iodide or methyl acetate. They are mainly saturated or unsaturated hydrocarbons, or occasionally contain an oxygen atom or an iodine atom in the molecule. Japan Patent Laid Open No. 04-295445 discloses a technology, by which for removing the alkanes an organic phase of the column top condensate of a lower boiling point component removal column is distilled in a distillation column (alkane removal column) to recycle the column top distillate liquid containing methyl iodide, methyl acetate, and a carbonyl impurity to a reactor, or feed the same to an acetaldehyde removal column, and water is added to the bottom fraction of the column bottom containing alkanes, water, and acetic acid for extraction to recycle the aqueous phase containing acetic acid to a reactor, and to discard the organic phase containing alkanes. However, the literature neither discloses nor suggests how to improve a potassium permanganate test value of the product acetic acid.

CITATION LIST

Patent Literature

Patent Literature 1: Japan Patent Laid Open No. 07-25813
Patent Literature 2: National Publication of International Patent Application No. 2001-508405
Patent Literature 3: Japan Patent Laid Open No. 04-295445

SUMMARY OF INVENTION

Technical Problem

Therefore, an object of the present invention is to provide a method capable of industrially and efficiently producing acetic acid having a good potassium permanganate test value without a large cost.

Solution to Problem

In order to attain the object, the present inventors have conducted diligent studies to discover that the crotonaldehyde concentration in the bottom fraction of a dehydration tower can be reduced and the potassium permanganate test value of the bottom fraction can be improved significantly by setting the reflux ratio of a lower boiling point component removal column at a value of not less than a specific value, as well as providing a distillation column (crotonaldehyde removal column) for treating an organic phase of the column top condensate of the lower boiling point component removal column, and specifying the operating conditions of the crotonaldehyde removal column in a carbonylation process of a methanol method. More precisely, since the boiling point of crotonaldehyde (104° C.) is lower than the boiling point of acetic acid (117° C.), when the reflux ratio of a lower boiling point component removal column is increased, crotonaldehyde is concentrated at the column top of the distillation column. When the concentrated crotonaldehyde is recycled to a reaction vessel, the same reacts with acetaldehyde in the reaction vessel to form 2-ethyl crotonaldehyde. Further, crotonaldehyde reacts with hydrogen in the reaction vessel to form butanol, which reacts with acetic acid to form butyl acetate. The influence of 2-ethyl crotonaldehyde on a potassium permanganate test value is weak compared to crotonaldehyde, and butanol and butyl acetate do not affect at all a potassium permanganate test value and are harmless. Therefore, the quality of acetic acid tends to be improved. Meanwhile, since the boiling points of 2-ethyl crotonaldehyde and butyl acetate are 137° C. and 126° C., respectively, which are higher than the boiling point of acetic acid (117° C.), when the reflux ratio of a lower boiling point component removal column is increased, the column top concentrations of these components are further reduced, and they may be recycled from the bottom of the lower boiling point component removal column to a reaction system to be concentrated there, or may be partially sent to the next step from a side cut at a position higher than a feeding position of a charging mixture, or contained in product acetic acid. Meanwhile, useful methyl iodide and unnecessary crotonaldehyde can be efficiently separated by performing a distillation treatment on the column top condensate of a lower boiling point component removal column, in which crotonaldehyde is concentrated, separately from an acetaldehyde removal treatment. Namely, for example, when an organic phase of the column top condensate of a lower boiling point component removal column is subjected to a distillation treatment, methyl iodide may be obtained together with methyl acetate as a column top distillate liquid. The same may be recycled to a decanter storing the column top condensate of a lower boiling point component removal column, or to a reaction vessel. Further, crotonaldehyde may be obtained as the column bottom fraction of the column bottom together with other high boiling point impurities (such as 2-ethyl crotonaldehyde, butyl acetate, and alkanes), and acetic acid. The bottom fraction is removed out of the system and discarded. Water may be concentrated at the column top or withdrawn from the column bottom. In this regard, a heretofore known alkane removal column may be utilized as a crotonaldehyde removal column. An alkane removal column may be operated continuously in some cases, but may be also operated batchwise in a case where the formation speed of alkanes is slow. In the case of a batchwise operation the potassium permanganate test value of product acetic acid is deteriorated, and therefore the product quality is required to be maintained by an acetaldehyde removal treatment, ozonization, a change in an operating condition, or the like. There exists also a small amount of 2-ethyl crotonaldehyde at the column top of a lower boiling point component removal column, which may be discharged out of the system by the above operations similarly to crotonaldehyde, so that the potassium permanganate test value may be improved. However, the effect is limited, because 2-ethyl crotonaldehyde with a high boiling point is hardly concentrated at the column top of a lower boiling point component removal column. In this regard, mainly an organic phase of the column top condensate of a lower boiling point component removal column is fed to a crotonaldehyde removal column, but in addition thereto, or in place thereof, also an aqueous phase of the column top condensate of a lower boiling point component removal column may be fed to the crotonaldehyde removal column. Since, as described above, the potassium permanganate test value of product acetic acid may be improved simply, omission or downsizing of an acetaldehyde removal apparatus, or an ozonization apparatus, and reduction of a steam and electricity costs may be plotted. The present invention has been completed based on such findings as well as additional investigations.

Namely, the present invention provides a method for producing acetic acid comprising:

a carbonylation reaction step of reacting methanol with carbon monoxide in the presence of a catalyst system containing a metal catalyst and methyl iodide, as well as acetic acid, methyl acetate, and water in a reaction vessel to produce acetic acid;

an evaporation step of separating a reaction mixture obtained in the carbonylation reaction step into a vapor stream and a residual liquid stream in an evaporator;

a lower boiling point component removal step of separating the vapor stream by a first distillation column into a first overhead stream rich in at least one lower boiling point component selected from methyl iodide, and acetaldehyde, and a first acetic acid stream rich in acetic acid, and condensing and separating the first overhead stream to obtain an aqueous phase and an organic phase;

a first overhead stream recycle step of recycling at least a portion of the aqueous phase and/or organic phase to a reaction vessel; and a crotonaldehyde removal step of separating and removing crotonaldehyde by treating at least another portion of the aqueous phase and/or organic phase by a distillation column;

wherein with respect to a reflux ratio of the first distillation column, when only the aqueous phase is refluxed to the first distillation column, a reflux ratio of the aqueous phase is not less than 2, when only the organic phase is refluxed, a reflux ratio of the organic phase is not less than 1, and when both the aqueous phase and the organic phase are refluxed, a total reflux ratio of the aqueous phase and the organic phase is not less than 1.5; and in the crotonaldehyde removal step the distillation column is operated such that at least one of the following conditions (i) to (iii) is satisfied:

(i) the reflux ratio of the distillation column is not less than 0.01;

(ii) a ratio of the crotonaldehyde concentration (ppm by mass) in a distillate liquid of the distillation column to the crotonaldehyde concentration (ppm by mass) in a charging mixture (former/latter) is less than 1; and (iii) a ratio of the crotonaldehyde concentration (ppm by mass) in a bottom fraction of the distillation column to the crotonaldehyde concentration (ppm by mass) in a charging mixture (former/latter) is more than 1.

The method for producing acetic acid may further comprise a dehydration step of separating the first acetic acid stream by a second distillation column into a second overhead stream rich in water and a second acetic acid stream more enriched with acetic acid than the first acetic acid stream. In this case, the reflux ratio of the second distillation column is preferably not less than 0.3. In the second acetic acid stream the crotonaldehyde concentration may be not more than 0.98 ppm by mass, and/or the 2-ethyl crotonaldehyde concentration may be not more than 1.0 ppm by mass, and/or the butyl acetate concentration may be not more than 15 ppm by mass. Further, the potassium permanganate test value of the second acetic acid stream is preferably more than 50 minutes.

The catalyst system may further contain an ionic iodide.

The method for producing acetic acid may further comprise an acetaldehyde separation and removal step of separating and removing acetaldehyde by distilling at least a portion of the aqueous phase and/or the organic phase obtained by condensing the first overhead stream. In this case, at least a portion of a residual liquid after separating and removing acetaldehyde from at least a portion of the aqueous phase and/or the organic phase may be recycled to the reaction vessel.

In the vapor stream fed to the first distillation column the crotonaldehyde concentration may be 0 to 5.0 ppm by mass, and/or the 2-ethyl crotonaldehyde concentration may be 0 to 3.0 ppm by mass, and/or the butyl acetate concentration may be 0.1 to 13.0 ppm by mass.

In the first acetic acid stream the crotonaldehyde concentration may be not more than 1.3 ppm by mass, and/or the 2-ethyl crotonaldehyde concentration may be not more than 1.0 ppm by mass, and/or the butyl acetate concentration may be not more than 15 ppm by mass.

The crotonaldehyde concentration in a distillation column charging mixture in the crotonaldehyde removal step is, for example, 0.01 to 50 ppm by mass.

In the crotonaldehyde removal step the distillation column is preferably operated such that all the conditions (i) to (iii) are satisfied.

Distillation may be performed by a batch process in the crotonaldehyde removal step.

The throughput of the distillation column in the crotonaldehyde removal step is, for example, 0.0001 to 50 parts by mass with respect to an amount of the vapor stream fed to the first distillation column of 100 parts by mass.

Advantageous Effects of Invention

Since crotonaldehyde can be efficiently removed according to the present invention by setting the reflux ratio of a lower boiling point component removal column at a value of not less than a specific value, and using a crotonaldehyde removal step, high quality acetic acid with a satisfactory potassium permanganate test value (hereinafter also referred to as "permanganate time", or "chameleon time") can be produced efficiently in an industrial scale without installing a large scale acetaldehyde removal apparatus or an ozonization apparatus.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

DESCRIPTION OF EMBODIMENTS

A method for producing acetic acid according to the present invention comprises a carbonylation reaction step of reacting methanol with carbon monoxide in the presence of a catalyst system containing a metal catalyst and methyl iodide, as well as acetic acid, methyl acetate, and water in a reaction vessel to produce acetic acid; an evaporation step of separating a reaction mixture obtained in the carbonylation reaction step into a vapor stream and a residual liquid stream in an evaporator; a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase; a first overhead stream recycle step of recycling at least a portion of the aqueous phase and/or organic phase to a reaction vessel; and a crotonaldehyde removal step of separating and removing crotonaldehyde by treating at least another portion of the aqueous phase and/or organic phase by a distillation column; and with respect to a reflux ratio of the first distillation column, when only the aqueous phase is refluxed to the first distillation column, a reflux ratio of the aqueous phase is not less than 2, when only the organic phase is refluxed, a reflux ratio of the organic phase is not less than 1, and when both the aqueous phase and the organic phase are refluxed, a total reflux ratio of the aqueous phase and the organic phase is not less than 1.5; and in the crotonaldehyde removal step the distillation column (crotonaldehyde removal column) is operated such that at least one of the following conditions (i) to (iii) is satisfied:

(i) the reflux ratio of the distillation column is not less than 0.01;

(ii) a ratio of the crotonaldehyde concentration (ppm by mass) in a distillate liquid of the distillation column to the crotonaldehyde concentration (ppm by mass) in a charging mixture (feeding liquid) (former/latter) is less than 1; and (iii) a ratio of the crotonaldehyde concentration (ppm by mass) in a bottom fraction of the distillation column to the crotonaldehyde concentration (ppm by mass) in a charging mixture (feeding liquid) (former/latter) is more than 1.

According to the present invention, the reflux ratio of the first distillation column is increased to concentrate crotonaldehyde at the column top, and at least a portion of an aqueous phase and/or an organic phase of a column top condensate of a lower boiling point component removal column, in which crotonaldehyde is concentrated, is recycled to a reaction vessel. Since crotonaldehyde is concentrated at the column top, the crotonaldehyde concentration in the first acetic acid stream is decreased, and as the result product acetic acid having a good potassium permanganate test value may be obtained. Further, since crotonaldehyde recycled to a reaction vessel is transformed to 2-ethyl crotonaldehyde having a weaker influence on a potassium permanganate test value or butyl acetate having absolutely no influence thereon due to the reactions of crotonaldehyde+acetaldehyde→2-ethyl crotonaldehyde, crotonaldehyde+hydrogen→butyl alcohol, butyl alcohol+acetic acid→butyl acetate, the quality of product acetic acid may be improved. Further, by treating in a crotonaldehyde removal column at least another portion of the aqueous phase and/or organic phase of the column top condensate of a lower boiling point component removal column, in which crotonaldehyde is concentrated, according to the present invention, since the boiling point of crotonaldehyde is as high as 104° C., it may be withdrawn and discharged out of the system as a high boiling point compound in a bottom fraction side together with acetic acid or alkanes, so that the potassium permanganate test value of product acetic acid may be further improved. Since the column top condensate of the crotonaldehyde removal column contains a useful component (such as methyl iodide, and methyl acetate), it may be recycled to a decanter storing the column top condensate of the lower boiling point component removal column, or a reaction vessel.

With respect to the reflux ratio of the first distillation column, when only the aqueous phase is refluxed to the first distillation column, the reflux ratio of the aqueous phase (amount of the aqueous phase refluxed/amount of the distillate of the aqueous phase) is not less than 2, preferably not less than 3, more preferably not less than 5, further preferably not less than 8, and particularly preferably not less than 12. When only the organic phase is refluxed to the first distillation column, the reflux ratio of the organic phase (amount of the organic phase refluxed/amount of the distillate of the organic phase) is not less than 1, preferably not less than 1.5, more preferably not less than 2, further preferably not less than 4, and particularly preferably not less than 5. Further, when both the aqueous phase and the organic phase are refluxed to the first distillation column, the total reflux ratio of the aqueous phase and the organic phase (total amount of the aqueous phase and the organic phase refluxed/total amount of the distillate of the aqueous phase and the organic phase) is not less than 1.5, preferably not less than 2.3, more preferably not less than 3.5, further preferably not less than 6, and particularly preferably not less than 8.5. Further, when the aqueous phase is refluxed to the first distillation column, the reflux ratio of the aqueous phase (amount of the aqueous phase refluxed/amount of the distillate of the aqueous phase) is preferably not less than 2, more preferably not less than 3, further preferably not less than 5, particularly preferably not less than 8, and especially not less than 12. In any cases, the upper limit of the reflux ratio of the first distillation column may be, for example, 3000 (particularly 1000), or may be 100 (particularly 30).

In (i) above, the reflux ratio of the crotonaldehyde removal column is preferably not less than 0.05, more preferably not less than 0.5, further preferably not less than 5, and particularly preferably not less than 20 (for example, not less than 30). The upper limit of the reflux ratio of the crotonaldehyde removal column is, for example, 1000. In (ii) above, the ratio of the crotonaldehyde concentration (ppm by mass) in a distillate liquid of the crotonaldehyde removal column to the crotonaldehyde concentration (ppm by mass) in a charging mixture (former/latter) is preferably not more than 0.95, more preferably not more than 0.80, further preferably not more than 0.70, and particularly preferably not more than 0.60 (for example, not more than 0.50, especially not more than 0.30, and among others not more than 0.20). In (iii) above, the ratio of the crotonaldehyde concentration (ppm by mass) in a bottom fraction of the crotonaldehyde removal column to the crotonaldehyde concentration (ppm by mass) in a charging mixture (former/latter) is preferably not less than 1.2, more preferably not less than 1.5, further preferably not less than 2.0, particularly preferably not less than 3.0 (for example, not less than 4.0, and especially not less than 5.0), and among others not less than 10 (for example, not less than 20). When the crotonaldehyde removal column is operated such that at least one of the above conditions (i) to (iii) is satisfied, crotonaldehyde is concentrated at the column bottom and may be discharged as a bottom fraction together with acetic acid and other high boiling point impurities such as an alkane out of the system.

The method for producing acetic acid may comprise a dehydration step of separating the first acetic acid stream by a second distillation column into a second overhead stream rich in water and a second acetic acid stream more enriched with acetic acid than the first acetic acid stream. Through dehydration of the first acetic acid stream in the second distillation column, a second acetic acid stream with a low water content is obtainable as a bottom fraction or a side cut liquid from the column bottom or a middle site of the column. The second acetic acid stream may be used as product acetic acid as it is, or if necessary after additional purification.

The reflux ratio of the second distillation column is for example, not less than 0.3, preferably not less than 1.0, more preferably not less than 5.0, and further preferably not less than 10 (for example, not less than 12). The upper limit of the reflux ratio of the second distillation column is, for example, 3000 (or 1000), or on the order of 200 (or 100). By increasing the reflux ratio of the second distillation column to not less than 0.3, the purity and the potassium permanganate test value of the second acetic acid stream can be improved.

The crotonaldehyde concentration in the second acetic acid stream is, for example, not more than 0.98 ppm by mass, preferably not more than 0.80 ppm by mass, more preferably not more than 0.50 ppm by mass, and further preferably not more than 0.30 ppm by mass. When the crotonaldehyde concentration in the second acetic acid stream is set at not more than 0.98 ppm by mass, the crotonaldehyde concentration in the second acetic acid stream can be significantly reduced, and at the same time the potassium permanganate test value of the second acetic acid stream can be improved remarkably. The lower limit of the crotonaldehyde concentration in the second acetic acid stream may be 0 ppm by mass, but also, for example, 0.01 ppm by mass (or 0.10 ppm by mass).

The 2-ethyl crotonaldehyde concentration in the second acetic acid stream is, for example, not more than 1.00 ppm by mass, preferably not more than 0.50 ppm by mass, more preferably not more than 0.30 ppm by mass, and further preferably not more than 0.20 ppm by mass. When the 2-ethyl crotonaldehyde concentration in the second acetic acid stream is set at not more than 1.0 ppm by mass, the potassium permanganate test value of the second acetic acid stream can be more improved. The lower limit of the 2-ethyl crotonaldehyde concentration in the second acetic acid stream may be, for example, 0 ppm by mass, or 0.01 ppm by mass (for example, 0.10 ppm by mass).

The butyl acetate concentration in the second acetic acid stream is, for example, not more than 15 ppm by mass, preferably not more than 10 ppm by mass, more preferably not more than 8 ppm by mass, and particularly preferably not more than 5 ppm by mass (for example, not more than 3 ppm by mass). When the butyl acetate concentration in the second acetic acid stream is set at not more than 15 ppm by mass, the purity of the second acetic acid stream can be improved. The lower limit of the butyl acetate concentration in the second acetic acid stream may be, for example, 0 ppm by mass, or 0.1 ppm by mass (for example, 0.3 ppm by mass, or 1.0 ppm by mass).

The potassium permanganate test value of the second acetic acid stream is preferably more than 50 minutes, more preferably not less than 60 minutes, further preferably not less than 100 minutes, and particularly preferably not less than 120 minutes (for example, not less than 180 minutes, especially not less than 240 minutes, and among others not less than 360 minutes).

The catalyst system may further contain an ionic iodide. An ionic iodide functions as a co-catalyst.

The method for producing acetic acid may further comprise an acetaldehyde separation and removal step of separating and removing acetaldehyde by distilling at least a portion of the aqueous phase and/or the organic phase obtained by condensing the first overhead stream. In this case, at least a portion of a residual liquid after separating and removing acetaldehyde from at least a portion of the aqueous phase and/or the organic phase may be recycled to a reaction vessel. Through installation of an acetaldehyde separation and removal step, acetaldehyde formed ion a reaction system can be separated and removed efficiently. Further, by recycling the residual liquid after separating and removing acetaldehyde to a reaction vessel, methyl iodide etc., which are useful, may be utilized effectively.

The crotonaldehyde concentration in the vapor stream fed to the first distillation column is, for example, 0 to 5.0 ppm by mass (for example, 0.01 to 4.0 ppm by mass), preferably 0.1 to 3.0 ppm by mass, and further preferably 0.2 to 2.0 ppm by mass. The 2-ethyl crotonaldehyde concentration in the vapor stream is, for example, 0 to 3.0 ppm by mass (for example, 0.01 to 2.5 ppm by mass), preferably 0.02 to 2.0 ppm by mass, and further preferably 0.03 to 0.8 ppm by mass. The butyl acetate concentration in the vapor stream is, for example, 0.1 to 13.0 ppm by mass, preferably 0.2 to 12.0 ppm by mass, and further preferably 0.3 to 9.0 ppm by mass.

The crotonaldehyde concentration in the first acetic acid stream is, for example, not more than 1.3 ppm by mass, preferably not more than 1.0 ppm by mass, more preferably not more than 0.85 ppm by mass, and particularly preferably not more than 0.5 ppm by mass (for example, not more than 0.25 ppm by mass). When the crotonaldehyde concentration in the first acetic acid stream is set at not more than 1.3 ppm by mass, the crotonaldehyde concentration in the second acetic acid stream can be significantly reduced, and at the same time the potassium permanganate test value of the second acetic acid stream can be improved remarkably. The lower limit of the crotonaldehyde concentration in the first acetic acid stream may be 0 ppm by mass, but also, for example, 0.01 ppm by mass (or 0.10 ppm by mass).

The 2-ethyl crotonaldehyde concentration in the first acetic acid stream is, for example, not more than 1.0 ppm by mass, and preferably not more than 0.50 ppm by mass. When the 2-ethyl crotonaldehyde concentration in the first acetic acid stream is set at not more than 1.0 ppm by mass, the potassium permanganate test value of the second acetic acid stream can be more improved. The lower limit of the 2-ethyl crotonaldehyde concentration in the first acetic acid stream may be, for example, 0 ppm by mass, or 0.01 ppm by mass (or 0.10 ppm by mass).

The butyl acetate concentration in the first acetic acid stream is, for example, not more than 15 ppm by mass, preferably not more than 10 ppm by mass, more preferably not more than 8 ppm by mass, and particularly preferably not more than 5 ppm by mass (for example, not more than 3 ppm by mass). When the butyl acetate concentration in the first acetic acid stream is set at not more than 15 ppm by mass, the purity of the second acetic acid stream can be improved. The lower limit of the butyl acetate concentration in the first acetic acid stream may be, for example, 0 ppm by mass, or 0.1 ppm by mass (for example, 0.3 ppm by mass, or 1.0 ppm by mass).

The crotonaldehyde concentration in a distillation column charging mixture in the crotonaldehyde removal step is normally 0.01 to 50 ppm by mass (for example, 0.1 to 50 ppm by mass), preferably 0.3 to 30 ppm by mass, more preferably 0.5 to 10 ppm by mass, and further preferably 0.8 to 7.0 ppm by mass (for example, 1.0 to 5.0 ppm by mass).

In the crotonaldehyde removal step, the distillation column is preferably operated such that all the conditions (i) to (iii) are satisfied. By operating the crotonaldehyde removal column so as to satisfy all the conditions (i) to (iii), the removal efficiency for crotonaldehyde can be enhanced remarkably, and the potassium permanganate test value of product acetic acid can be improved remarkably.

Distillation in the crotonaldehyde removal step may be performed by a batch process. When a certain amount of crotonaldehyde has accumulated in the aqueous phase and/or organic phase, a batchwise distillation operation to be performed can make the energy cost to be saved.

The throughput of the distillation column in the crotonaldehyde removal step is, for example, 0.0001 to 50 parts by mass, and preferably 0.001 to 30 parts by mass (for example, 0.01 to 10 parts by mass, and particularly 0.1 to 5 parts by mass) with respect to an amount of the vapor stream fed to the first distillation column of 100 parts by mass.

Hereinafter, one embodiment of the present invention will be described. FIG. 1 is one example of an acetic acid production flow diagram (carbonylation process of a methanol method) showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, a distillation column 10, condensers 1a, 2a, 3a, 5a, 6a, and 10a, a heat exchanger 2b, reboilers 3b, 5b, 6b, and 10b, lines 11 to 56, 58 to 63, and a pump 57 and is configured to be capable of continuously producing acetic acid. In the method for producing acetic acid according to the present embodiment, a reaction step, an evaporation step (flash step), a first distillation step, a second distillation step, a third distillation step, a crotonaldehyde removal step, and an adsorptive removal step are performed in the reaction vessel 1, the evaporator 2, the distillation column 3, the distillation column 5, the distillation column 6, the distillation column 10, and the ion exchange resin column 7, respectively. The first distillation step is also referred to as a lower boiling point component removal step, the second distillation step is also referred to as a dehydration step, and the third distillation step is also referred to as a higher boiling point component removal step. In the present invention, the steps are not limited to those described above and for example, equipment of the distillation column 5, the distillation column 6, the ion exchange resin column 7, the acetaldehyde separation and removal system 9 (acetaldehyde removal column, etc.) may be excluded. As mentioned later, a product column may be disposed downstream of the ion exchange resin column 7.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \quad (1)$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11.

Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^-$ can be used as the rhodium catalyst. For example, an iridium complex represented by the chemical formula $[Ir(CO)_2I_2]^{31}$  can be used as the iridium catalyst. A metal complex catalyst is preferred as the metal catalyst. The concentration (in terms of the metal) of the catalyst in the reaction mixture is, for example, 100 to 10000 ppm by mass, preferably 200 to 5000 ppm by mass, further preferably 400 to 2000 ppm by mass, with respect to the whole liquid phase of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. When, for example, an iridium catalyst is used, a ruthenium compound or an osmium compound may be also used as a co-catalyst. The total usage of such compounds is, for example, 0.1 to 30 mol (in terms of the metal), and preferably 0.5 to 15 mol (in terms of the metal) with respect to 1 mol of iridium (in terms of the metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, further preferably 1 to 6% by mass, particularly preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture.

Other examples of the by-products include hydrogen, methane, carbon dioxide, acetaldehyde, crotonaldehyde, 2-ethyl crotonaldehyde, butyl acetate, dimethyl ether, alkanes, formic acid, and propionic acid, and alkyl iodides such as ethyl iodide, propyl iodide, butyl iodide, hexyl iodide and decyl iodide.

The acetaldehyde concentration in a reaction mixture liquid is, for example, not more than 500 ppm by mass, preferably not more than 450 ppm by mass, more preferably not more than 400 ppm by mass, further preferably not more than 350 ppm by mass, and particularly preferably not more than 300 ppm by mass (for example, not more than 250 ppm by mass). The lower limit of the acetaldehyde concentration in a reaction mixture liquid is, for example, 1 ppm by mass (or 10 ppm by mass).

The crotonaldehyde concentration in a reaction mixture liquid is, for example, not more than 5 ppm by mass, preferably not more than 3 ppm by mass, and further preferably not more than 2 ppm by mass. The lower limit of the crotonaldehyde concentration in a reaction mixture liquid is 0 ppm, but may be, for example, 0.1 ppm by mass (or 0.2 ppm by mass). The 2-ethyl crotonaldehyde concentration in a reaction mixture liquid is, for example, not more than 5 ppm by mass, preferably not more than 3 ppm by mass, and further preferably not more than 2 ppm by mass. The lower limit of the 2-ethyl crotonaldehyde concentration in a reaction mixture liquid is 0 ppm, but may be, for example, 0.1 ppm by mass, or 0.2 ppm by mass.

According to the present invention the reflux ratio of a lower boiling point component removal column is controlled at a value of not less than a specific value for the sake of improvement of the potassium permanganate test value of product acetic acid as described above. When the reflux ratio of a lower boiling point component removal column is increased, crotonaldehyde is concentrated at the column top. When the concentrated crotonaldehyde is recycled to a reaction vessel, crotonaldehyde is hydrogenated to form butyl alcohol, and the butyl alcohol is converted to butyl acetate through a reaction with acetic acid, thereby becoming harmless to a potassium permanganate test. Therefore, the butyl acetate concentration in a reaction mixture liquid tends to increase according to the present invention. However, such increase in the butyl acetate concentration may occasionally lead to decrease in the purity of product acetic acid. Therefore, it is preferable to control the butyl acetate concentration in a reaction mixture liquid to, for example, 0.1 to 15 ppm by mass (particularly 1 to 12 ppm by mass, and especially 2 to 9 ppm by mass).

Also, the reaction mixture may contain a metal, such as iron, nickel, chromium, manganese, or molybdenum, generated by the corrosion of the apparatus [corroded metal (also referred to as "corrosion metal")], and other metals such as cobalt, zinc, and copper. The corroded metal and other metals are also collectively referred to as a "corroded metal, etc.".

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.6 MPa (absolute pressure), further preferably 0.9 to 1.4 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. Hydrogen is contained in carbon monoxide used as a raw material, and is also formed by a shift reaction ($CO+H_2O \rightarrow H_2+CO_2$) occurring in the reaction vessel 1. The hydrogen partial pressure in the reaction vessel 1 is, for example, not less than 0.01 MPa (absolute pressure), preferably not less than 0.015 MPa (absolute pressure), more preferably not less than 0.02 MPa (absolute pressure), further preferably not less than 0.04 MPa (absolute pressure), and particularly preferably not less than 0.06 MPa (absolute pressure) [for example, not less than 0.07 MPa (absolute pressure)]. In this regard, the upper limit of the hydrogen partial pressure in the reaction vessel 1 is, for example, 0.5 MPa (absolute pressure) [particularly 0.2 MPa (absolute pressure)]. When the hydrogen partial pressure in the reaction vessel becomes too high, increase in an amount of acetaldehyde formed, or increase in crotonaldehyde through aldol condensation may occur, and when the same is conversely too low, the reaction of crotonaldehyde→butanol substantially ceases to occur. The vapor of a gaseous phase portion in the reaction vessel 1 can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom part of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio.

A vapor generated in the present step contains, for example, methyl iodide, hydrogen iodide, water, methyl acetate, acetic acid, dimethyl ether, methanol, acetaldehyde, crotonaldehyde, 2-ethyl crotonaldehyde, butyl acetate, formic acid, propionic acid, and an alkyl iodide, such as ethyl iodide, propyl iodide, butyl iodide, hexyl iodide, and decyl iodide, and is withdrawn continuously from an evaporator 2 to line 17 (vapor stream discharge line). A portion of the vapor stream withdrawn from the evaporator 2 is continuously introduced to the condenser 2a, and another portion of the vapor stream is continuously introduced to the next distillation column 3 through the line 21. In the vapor stream, the acetic acid concentration is, for example, 50 to 85% by mass, and preferably 55 to 75% by mass; the methyl iodide concentration is, for example, 2 to 50% by mass (preferably 5 to 30% by mass); the water concentration is, for example, 0.2 to 20% by mass (preferably 1 to 15% by mass); and the methyl acetate concentration is, for example, 0.2 to 50% by mass (preferably 2 to 30% by mass). The crotonaldehyde concentration in the vapor stream is, for example, 0 to 5.0 ppm by mass (for example, 0.01 to 4.0 ppm by mass), preferably 0.1 to 3.0 ppm by mass, and further preferably 0.2 to 2.0 ppm by mass. The 2-ethyl crotonaldehyde concentration in the vapor stream is, for example, 0 to 3.0 ppm by mass (for example, 0.01 to 2.5 ppm by mass), preferably 0.02 to 2.0 ppm by mass, and further preferably 0.03 to 0.8 ppm by mass. The butyl acetate concentration in the vapor stream is, for example, 0.1 to 13 ppm by mass, preferably 0.2 to 12 ppm by mass, and further preferably 0.3 to 9 ppm by mass.

The residual liquid stream generated in this step contains, for example, the catalyst and the co-catalyst (methyl iodide, lithium iodide, etc.) contained in the reaction mixture, and water, methyl acetate, acetic acid, crotonaldehyde, 2-ethyl crotonaldehyde, butyl acetate, formic acid, and propionic acid remaining without being volatilized in this step, and is continuously introduced to the heat exchanger 2b from the evaporator 2 through the line 18 using the pump 57. The heat exchanger 2b cools the residual liquid stream from the evaporator 2. The cooled residual liquid stream is continuously introduced to the reaction vessel 1 from the heat exchanger 2b through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, crotonaldehyde, 2-ethyl crotonaldehyde, butyl acetate, formic acid, and propionic acid and is introduced to the reaction vessel 1 from the condenser 2a through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50.

In the inside of the distillation column 3, the column top pressure is set to, for example, 80 to 160 kPa (gauge pressure), and the column bottom pressure is higher than the column top pressure and is set to, for example, 85 to 180 kPa (gauge pressure). In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (preferably 125 to 160° C.)

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, crotonaldehyde, and formic acid. This vapor also contains acetic acid. Such a vapor is continuously introduced to the condenser 3a through the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, crotonaldehyde, and formic acid and is continuously introduced to the decanter 4 from the condenser 3a through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, crotonaldehyde, and formic acid. The organic phase contains, for example, methyl iodide and, for example, hydrogen iodide, water, methyl acetate, acetic acid, dimethyl ether, methanol, acetaldehyde, crotonaldehyde, and formic acid.

In the present embodiment, a portion of the aqueous phase is refluxed to the distillation column 3 through the line 29, and another portion of the aqueous phase is introduced to the reaction vessel 1 through the lines 29, 30, and 23 and recycled. A portion of the organic phase is introduced to the reaction vessel 1 through the lines 31 and 23 and recycled. Another portion of the organic phase and/or a remaining portion of the aqueous phase is introduced to the acetaldehyde separation and removal system 9 through the lines 31 and 50 and/or the lines 30 and 51. A portion of an organic phase may be refluxed to the distillation column 3 in addition to, or instead of a reflux of an aqueous phase.

The reflux ratio of the distillation column 3 will be described below. When only the aqueous phase of the condensate portion of the overhead stream (the first overhead stream) is refluxed to the distillation column 3, the reflux ratio of the aqueous phase (amount of the aqueous phase refluxed/amount of the distillate of the aqueous phase) is desirably, for example, not less than 2, preferably not less than 3, more preferably not less than 4, further preferably not less than 8, and particularly preferably not less than 10. When only the organic phase of the condensate portion of the overhead stream is refluxed to the distillation column 3, the reflux ratio of the organic phase (amount of the organic phase refluxed/amount of the distillate of the organic phase) is desirably, for example, not less than 1, preferably not less than 1.5, more preferably not less than 2, further preferably not less than 4, and particularly preferably not less than 5. Further, when both the aqueous phase and the organic phase of the condensate portion of the overhead stream are refluxed to the distillation column 3, the total reflux ratio of the aqueous phase and the organic phase (total amount of the aqueous phase and the organic phase refluxed/total amount of the distillate of the aqueous phase and the organic phase) is desirably, for example, not less than 1.5, preferably not less than 2.3, more preferably not less than 3, further preferably not less than 6, and particularly preferably not less than 7.5. Meanwhile, when an aqueous phase is refluxed to the distillation column 3, the reflux ratio of the aqueous phase (amount of the aqueous phase refluxed/amount of the distillate of the aqueous phase) is preferably not less than 2, more preferably not less than 3, further preferably not less than 5, particularly preferably not less than 8, and especially not less than 12. The upper limit of the reflux ratio of the distillation column 3 may be in any cases, for example, 3000 (particularly 1000), or may be 100 (particularly 30). Since crotonaldehyde (boiling point 104° C.) has a lower boiling point than that of acetic acid (boiling point 117° C.), crotonaldehyde is concentrated thicker at the column top of the distillation column 3 by increasing the reflux ratio of the distillation column 3, and therefore the crotonaldehyde concentration in a first acetic acid stream obtained for example as a side stream is decreased. When a condensed portion of a first overhead stream (aqueous phase and/or organic phase), in which crotonaldehyde is concentrated by increasing the reflux ratio of the distillation column 3, is recycled to the reaction vessel 1, crotonaldehyde reacts with acetaldehyde in the reaction vessel 1 to form 2-ethyl crotonaldehyde. Further, crotonaldehyde reacts with hydrogen in the reaction vessel 1 to form butanol, which reacts with acetic acid to form butyl acetate. The influence of 2-ethyl crotonaldehyde on a potassium permanganate test value is weak compared to crotonaldehyde, and butyl acetate does not affect at all a potassium permanganate test value. Therefore, the quality of acetic acid tends to be improved. Meanwhile, since the boiling points of 2-ethyl crotonaldehyde and butyl acetate are 137° C. and 126° C., respectively, and higher than the boiling point of acetic acid (117° C.), when the reflux ratio of the distillation column 3 is increased, its column top concentrations are reduced, and therefore they are apt to be concentrated in a side cut at a position higher than a feeding position of a charging mixture to the distillation column 3, or in the bottom fraction.

In the present Embodiment, a portion of the organic phase is introduced into a distillation column 10 (crotonaldehyde removal column) via lines 31, 50, and 58, where crotonaldehyde is separated and removed by distillation. The distillation may be conducted either continuously (continuous operation), or batchwise (batch process). In a case where the amount of crotonaldehyde formed in the reaction system is very small, it is preferable that crotonaldehyde be separated and removed by a batch process, when a certain amount of crotonaldehyde is accumulated in the aqueous phase and/or the organic phase, for the sake of reduction of the energy cost and the like. In the case of a continuous operation, both quality maintenance and steam reduction can be attained by changing the throughput (amount fed). The throughput of the distillation column 10 (crotonaldehyde removal column) may be, for example, 0.0001 to 50 parts by mass (for example, 0.001 to 30 parts by mass), or may be also 0.01 to 10 parts by mass (for example, 0.1 to 5 parts by mass), with respect to of an amount fed to the distillation column 3 (first distillation column; lower boiling point component removal column) of 100 parts by mass. The distillation column 10 consists of, for example, a distillation column, such as a plate column and a packed column. The theoretical number of plates of the distillation column 10 is, for example, 1 to 100 plates, preferably 2 to 50 plates, more preferably 4 to 30 plates, and further preferably 5 to 20 plates (for example, 6 to 15 plates). In a case where distillation is conducted continuously, the feeding position of a feeding liquid to the distillation column 10 is preferably at a middle position of the distillation column in the height direction (between the first plate from the column top and the first plate from the column bottom), and may be at a position approximately 20% to 80% (2/10 to 8/10) downward from the top. If the feeding position is too low, the loss of methyl iodide increases, and if it is too high, the amount of crotonaldehyde removed (and the amount of alkanes removed) decreases. The crotonaldehyde concentration in a feeding liquid (charging mixture) to the distillation column 10 is normally 0.01 to 50 ppm by mass (for example, 0.1 to 50 ppm by mass), preferably 0.3 to 30 ppm by mass, more preferably 0.5 to 10 ppm by mass, and further preferably 0.8 to 7.0 ppm by mass (for example, 1.0 to 5.0 ppm by mass). The column top vapor of the distillation column 10 is introduced into a condenser 10a via a line 59, and condensed. A portion of the condensate is refluxed to the distillation column 10 via a line 61, and the remaining portion of the condensate is withdrawn as the distillate liquid via a line 62. The distillate liquid contains mainly methyl iodide, and methyl acetate, and also dimethyl ether, lower boiling point alkanes, etc. The distillate liquid may be recycled to, for example, the decanter 4, or the reaction vessel 1. A gas component in the column top vapor which is not condensed in the condenser 10a is sent, for example, to a scrubber system 8 via a line 63. From the column bottom of the distillation column 10, a bottom fraction is withdrawn via a line 60. The bottom fraction contains mainly high boiling point impurities, such as crotonaldehyde, 2-ethyl crotonaldehyde, butyl acetate, and alkanes, and acetic acid. The bottom fraction is normally discarded. A very small amount of water contained in the organic phase may be concentrated at the column top, or withdrawn from the column bottom. The aqueous phase may be introduced to the distillation column 10 via lines 30, 51, and 58 in addition to, or instead of introduction of the organic phase into the distillation column 10. In this case, a distillate liquid containing water is obtained from the column top of the distillation column 10, and a bottom fraction containing a high boiling point impurity such as crotonaldehyde, and acetic acid is obtained from the column bottom. As described above, by treating the aqueous phase and/or the organic phase in the distillation column 10, crotonaldehyde may be removed efficiently, so that the potassium permanganate test value of product acetic acid may be improved. Therefore, omission or downsizing of a large-scale apparatus such as an ozonization apparatus, and reduction of a steam and electricity costs may be plotted. The reflux ratio (amount refluxed/amount of the distillate) of the distillation column 10 is, for example, not less than 0.01, preferably not less than 0.05, more preferably not less than 0.5, further preferably not less than 5, and particularly preferably not less than 20 (for example, not less than 30). The upper limit of the reflux ratio of the distillation column 10 is, for example, 1000 (or 100). When the reflux ratio of the distillation column 10 is too high, crotonaldehyde concentrated at the column bottom is concentrated conversely at the column top, so that the concentration of acetic acid having a higher boiling point increases. Therefore, the reflux ratio of the distillation column 10 is preferably not more than 100. Since crotonaldehyde is withdrawn from the column bottom, the ratio of the crotonaldehyde concentration (ppm by mass) in the distillate liquid of the distillation column 10 to the crotonaldehyde concentration (ppm by mass) in a charging mixture (former/latter) is, for example, less than 1, preferably not more than 0.95, more preferably not more than 0.80, further preferably not more than 0.70, particularly preferably not more than 0.60 (for example, not more than 0.50, especially not more than 0.30, and among others not more than 0.20). Further, the ratio of the crotonaldehyde concentration (ppm by mass) in the bottom fraction of the distillation column 10 to the crotonaldehyde concentration (ppm by mass) in a charging mixture (former/latter) is, for example, more than 1, preferably not less than 1.2, more preferably not less than 1.5, further preferably not less than 2.0, particularly preferably not less than 3.0 (for example, not less than 4.0, and especially not less than 5.0), and among others not less than 10 (for example, not less than 20).

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91a. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93a. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91a. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93a. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system.

The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, further preferably 3 to 30, particularly preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95*a* through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97*a* through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation. The vapor at the column top is led to a condenser 98*a* through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.) miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94*a* through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas that has not been condensed in the condenser 94*a*, 97*a*, or 98*a* (line 211, 221, or 227) is subjected to absorption treatment in the scrubber system 8, or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95a through the line 208 without the medium of the decanter 95, cooled, and fed to the decanter 96. The other points are the same as in the example of FIG. 4.

In FIG. 1 described above, the gaseous portion generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, 2-ethyl crotonaldehyde, butyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. The first acetic acid stream contains in addition to acetic acid, for example, methyl iodide, hydrogen iodide, water, methyl acetate, dimethyl ether, methanol, acetaldehyde, crotonaldehyde, 2-ethyl crotonaldehyde, butyl acetate, formic acid, and propionic acid, as well as an alkyl iodide, such as ethyl iodide, propyl iodide, butyl iodide, hexyl iodide, and decyl iodide. In the first acetic acid stream, the methyl iodide concentration is, for example, 0.1 to 8% by mass, and preferably 0.2 to 5% by mass; the water concentration is, for example, 0.1 to 8% by mass, and preferably 0.2 to 5% by mass; and the methyl acetate concentration is, for example, 0.1 to 8% by mass, and preferably 0.2 to 5% by mass.

Since the reflux ratio of the first distillation column is set at a value of not less than a specific value, according to the present invention, crotonaldehyde is concentrated at the column top of the distillation column. Therefore, the crotonaldehyde concentration in the first acetic acid stream withdrawn as a side stream of the first distillation column is low. The crotonaldehyde concentration in the first acetic acid stream is, for example, not more than 1.3 ppm by mass, preferably not more than 1.0 ppm by mass, more preferably not more than 0.85 ppm by mass, and particularly preferably not more than 0.5 ppm by mass (for example, not more than 0.25 ppm by mass). When the crotonaldehyde concentration in the first acetic acid stream is not more than 1.3 ppm by mass, the crotonaldehyde concentration in the second acetic acid stream described below can be decreased remarkably and the potassium permanganate test value of the second acetic acid stream can be improved to a large extent. The lower limit of the crotonaldehyde concentration in the first acetic acid stream may be 0 ppm by mass, but may be also, for example, 0.01 ppm by mass (or 0.10 ppm by mass). The 2-ethyl crotonaldehyde concentration in the first acetic acid stream is, for example, not more than 1.0 ppm by mass, and preferably not more than 0.50 ppm by mass. When the 2-ethyl crotonaldehyde concentration in the first acetic acid stream is not more than 1.0 ppm by mass, the potassium permanganate test value of the second acetic acid stream described below can be more improved. The lower limit of the 2-ethyl crotonaldehyde concentration in the first acetic acid stream may be, for example, 0 ppm by mass, or may be 0.01 ppm by mass (or 0.10 ppm by mass). The butyl acetate concentration in the first acetic acid stream is, for example, not more than 15 ppm by mass, preferably not more than 10 ppm by mass, more preferably not more than 8 ppm by mass, and particularly preferably not more than 5 ppm by mass (for example, not more than 3 ppm by mass). When the butyl acetate concentration in the first acetic acid stream is not more than 15 ppm by mass, the purity of the second acetic acid stream described below can be improved. The lower limit of the butyl acetate concentration in the first acetic acid stream may be, for example, 0 ppm by mass, or 0.1 ppm by mass (for example, 0.3 ppm by mass, or 1.0 ppm by mass).

The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27.

A bottom fraction withdrawn from the column bottom of the distillation column 3, or a first acetic acid stream withdrawn as a side stream from the distillation column 3 may be used as it is as product acetic acid insofar as the quality is acceptable.

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. As a material for the distillation column 5 (at least a material for a liquid contact part and gas contact part), a nickel base alloy or zirconium is preferable. When such a material is used, corrosion of the inside of the distillation column by hydrogen iodide or acetic acid may be suppressed and elution of a corroded metal ion may be suppressed.

A charging mixture to the distillation column 5 includes at least a portion of the first acetic acid stream (line 27) and may include additionally a stream other than the first acetic acid stream [for example, a recycle stream from a downstream step (for example, line 42)].

The distillation column 5 consists of, for example, a distillation column such as a plate column or a packed column. In the case of adopting a plate column as the distillation column 5, the theoretical number of plates thereof is, for example, 5 to 50. The reflux ratio of the distillation column 5 is, for example, not less than 0.3, preferably not less than 1.0, more preferably not less than 5.0, and further preferably not less than 10 (for example, not less than 12). The upper limit of the reflux ratio of the distillation column 5 may be, for example, 3000 (or 1000), or on the order of 200 (or 100). When the reflux ratio of the distillation column 5 is not less than 0.3, since the boiling point of crotonaldehyde is lower than that of acetic acid, crotonaldehyde flown into the distillation column 5 may be concentrated at the column top, such that the crotonaldehyde concentration in a second acetic acid stream obtained as a side stream or a bottom stream may be reduced significantly. Further, when an overhead stream at the column top of the distillation column 5 (second overhead stream), in which crotonaldehyde has been concentrated, is recycled to the reaction vessel 1, crotonaldehyde is transformed to 2-ethyl crotonaldehyde which is least harmful, and butyl acetate which is harmless to the potassium permanganate test value as described above, and therefore the quality of acetic acid is more improved.

Inside the distillation column 5 in the second distillation step, the column top pressure is, for example, 0.10 to 0.28 MPa (gage pressure), preferably 0.15 to 0.23 MPa (gage pressure), and further preferably 0.17 to 0.21 MPa (gage pressure). The column bottom pressure is higher than the column top pressure, and is for example, 0.13 to 0.31 MPa (gage pressure), preferably 0.18 to 0.26 MPa (gage pressure), and further preferably 0.20 to 0.24 MPa (gage pressure). Inside the distillation column 5 in the second distillation step, preferably the column top temperature is less than 165° C., and the column bottom temperature is less than 175° C. When the column top temperature and the column bottom temperature in the distillation column 5 are in the above ranges, corrosion of the inside of the distillation column by hydrogen iodide or acetic acid may be more suppressed, and elution of a corroded metal ion may be more suppressed. The column top temperature is more preferably less than 163° C., further preferably less than 161° C., particularly preferably less than 160° C., and especially preferably less than 155° C. The lower limit of the column top temperature is, for example, 110° C. The column bottom temperature is more preferably less than 173° C., further preferably less than 171° C., and particularly preferably less than 166° C. The lower limit of the column bottom temperature is, for example, 120° C.

A vapor as an overhead stream (the second overhead stream) is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, crotonaldehyde, and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

A bottom fraction withdrawn from the column bottom of the distillation column 5, or a side stream withdrawn from a middle position of the column (second acetic acid stream) is enriched with acetic acid compared to the first acetic acid stream introduced continuously into the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. In the present embodiment, in the case of withdrawing a side stream, the withdrawal position of the side stream from the distillation column 5 is lower than the introduction position of the first acetic acid stream to the distillation column 5 in the height direction of the distillation column 5.

Since a second acetic acid stream has a high potassium permanganate test value according to the present invention, the same may be used as it is as product acetic acid. However the same may contain a very small amount of impurities [such as crotonaldehyde, 2-ethyl crotonaldehyde, butyl acetate, propionic acid, potassium acetate (in a case where potassium hydroxide is fed to a line 27 etc.), hydrogen iodide, and an entrained catalyst or co-catalyst described above]. Therefore, the bottom fraction or the side stream may be introduced continuously via a line 34 to a distillation column 6 and distilled.

The crotonaldehyde concentration in the second acetic acid stream is, for example, not more than 0.98 ppm by mass, preferably not more than 0.80 ppm by mass, more preferably not more than 0.50 ppm by mass, further preferably not more than 0.30 ppm by mass, and particularly especially preferably not more than 0.17 ppm by mass. When the crotonaldehyde concentration in the second acetic acid stream is set at not more than 0.98 ppm by mass, the crotonaldehyde concentration in the second acetic acid stream can be significantly reduced, and at the same time the potassium permanganate test value of the second acetic acid stream can be improved remarkably. The lower limit of the crotonaldehyde concentration in the second acetic acid stream may be 0 ppm by mass, but also, for example, 0.01 ppm by mass (or 0.10 ppm by mass). The 2-ethyl crotonaldehyde concentration in the second acetic acid stream is, for example, not more than 1.0 ppm by mass, preferably not more than 0.50 ppm by mass, more preferably not more than 0.30 ppm by mass, and further preferably not more than 0.20 ppm by mass. When the 2-ethyl crotonaldehyde concentration in the second acetic acid stream is set at not more than 1.0 ppm by mass, the potassium permanganate test value of the second acetic acid stream can be more improved. The lower limit of the 2-ethyl crotonaldehyde concentration in the second acetic acid stream may be, for example, 0 ppm by mass, or 0.01 ppm by mass (for example, 0.10 ppm by mass).

The butyl acetate concentration in the second acetic acid stream is, for example, not more than 15 ppm by mass, preferably not more than 10 ppm by mass, more preferably not more than 8 ppm by mass, and particularly preferably not more than 5 ppm by mass (for example, not more than 3 ppm by mass). When the butyl acetate concentration in the second acetic acid stream is set at not more than 15 ppm by mass, the purity of the second acetic acid stream can be improved. The lower limit of the butyl acetate concentration in the second acetic acid stream may be, for example, 0 ppm by mass, or 0.1 ppm by mass (for example, 0.3 ppm by mass, or 1.0 ppm by mass).

The potassium permanganate test value of the second acetic acid stream is preferably beyond 50 minutes, more preferably not less than 60 minutes, further preferably not less than 100 minutes, and particularly preferably not less than 120 minutes (for example, not less than 180 minutes, especially not less than 240 minutes, and among others not less than 360 minutes).

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. Meanwhile, this is not an indispensable step in the present Embodiment. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, the column top pressure is set to, for example, −100 to 150 kPa (gauge pressure), and the column bottom pressure is higher than the column top pressure and is set to, for example, −90 to 180 kPa (gauge pressure). In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled to the first acetic acid stream in the line 27 before introduction to the distillation column 5 from the condenser 6a through the lines 40, 41, and 42. Together with this or instead of this, a portion (distillate) of the condensate portion may be recycled to the vapor stream in the line 21 before introduction to the distillation column 3 from the condenser 6a through the lines 40, 41, and 43. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

A bottom fraction withdrawn via a line 39 from the column bottom of the distillation column 6 contains components with a boiling point higher than that of acetic acid (higher boiling point components) in an amount larger than in the overhead stream from the distillation column 6, including, for example, propionic acid, and an acetate such as potassium acetate (in a case where an alkali such as potassium hydroxide is fed to a line 34 and the like). Also, the bottom fraction withdrawn from the column bottom of the distillation column 6 through the line 39 also contains, for example, a corroded metal such as a metal formed at and released from the inside wall of a member constituting this acetic acid production apparatus, and a compound of iodine derived from corrosive iodine and the corroded metal, etc. In the present embodiment, such a bottom fraction is discharged to the outside of the acetic acid production apparatus.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be use in place of the distillation column 6. Since especially acetic acid having a very high potassium permanganate test value is obtainable by a distillation treatment in the distillation column 5 according to the present invention, the distillation column 6 may be omitted.

An ion exchange resin column 7 is a purification unit for conducting an adsorptive removal step. The adsorptive removal step is a step for further purifying acetic acid through adsorptive and removal of mainly an alkyl iodide (such as ethyl iodide, propyl iodide, butyl iodide, hexyl iodide, and decyl iodide) contained in a very small amount in a third acetic acid stream introduced continuously into an ion exchange resin column 7. In this regard, a second acetic acid stream from the distillation column 5 may be fed to the ion exchange resin column 7 omitting the distillation column 6. The adsorptive removal step using an ion exchange resin column 7 is not indispensable.

In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per $m^3$ resin volume $(m^3/h)$] is, for example, 3 to 15 $m^3/h \cdot m^3$ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, the column top pressure is set to, for example, −195 to 150 kPa (gauge pressure), and the column bottom pressure is higher than the column top pressure and is set to, for example, −190 to 180 kPa (gauge pressure). In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

EXAMPLES

Hereinafter, the present invention will be described in more detail with reference to Examples. However, the present invention is not intended to be limited by these Examples. In this regard, parts, %, ppm, ppb are all based on mass. A water concentration was measured by the Karl Fischer water determination method; a metal ion concentration was measured by ICP analysis (or atomic adsorption analysis); and concentrations of other components were measured by gas chromatography.

Comparative Example 1

The following experiments were carried out at a methanol method acetic acid pilot plant (see FIG. 1).

In an evaporator, Four hundred parts of a reaction mixture liquid [Composition: 7.8% of methyl iodide (MeI), 2.1% of methyl acetate (MA), 2.5% of water ($H_2O$), 910 ppm of a rhodium complex (in terms of Rh), 14.1% of lithium iodide (LiI), 250 ppm of acetaldehyde (AD), 1.3 ppm of crotonaldehyde (CR), 1.5 ppm of 2-ethyl crotonaldehyde (2ECR), 250 ppm of propionic acid (PA), 40 ppm of formic acid (FA), 4.5 ppm of butyl acetate (BA), and acetic acid as a balance (however, a very small amount of impurities were contained)] obtained in a reaction vessel [total pressure of 2.8 MPa (absolute pressure), carbon monoxide partial pressure of 1.4 MPa (absolute pressure), hydrogen partial pressure of 0.04 MPa (absolute pressure), and reaction temperature of 187° C.] were fed to the evaporator, and the evaporator was heated to evaporate 25% of the same (evaporation rate: 25%). One hundred parts of the vapor of the evaporator [Composition: 28.1% of methyl iodide, 4.9% of methyl acetate, 1.9% of water, 651 ppm of acetaldehyde, 1.4 ppm of crotonaldehyde, 0.22 ppm of 2-ethyl crotonaldehyde, 73 ppm of propionic acid, 85 ppm of formic acid, 0.6 ppm of butyl acetate, and acetic acid as a balance (however, a very small amount of impurities were contained)] were fed to a lower boiling point component removal column [20 actual plates, feeding position: the second plate from the bottom, column top pressure of 250 kPa (absolute pressure), and column top temperature of 140° C.]. The column top vapor was condensed and separated to an aqueous phase and an organic phase in a decanter, and then a portion of the organic phase (11 parts) was sent to an acetaldehyde removal column [80 actual plates, feeding position: the eleventh plate from the bottom, column top pressure of 280 kPa (absolute pressure), and column top temperature of 52° C.] to separate acetaldehyde, which was then discharged out of the system. The bottom fraction after the acetaldehyde removal (11 parts, nearly equivalent to the charging mixture) was recycled to the reaction system. The remaining portion of the organic phase (41 parts) was recycled directly to the reaction vessel. A portion of the aqueous phase was refluxed to the lower boiling point component removal column, and the remaining portion (1.5 parts) was recycled to the reaction vessel as a distillate liquid. The amount refluxed/amount of the distillate of the aqueous phase was defined as a reflux ratio, which was set at 2. Three parts of the bottom fraction were withdrawn from the column bottom of the lower boiling point component removal column and recycled to the reaction system. Sixty-five parts were withdrawn as a side cut (SC) stream from a middle part (the fourth plate from the bottom) of the lower boiling point component removal column and fed to a dehydration column [50 actual plates, feeding position: the thirty-fourth plate from the bottom, column top pressure of 295 kPa (absolute pressure), and column top temperature of 150° C.] A portion of the column top vapor condensate of the dehydration column was refluxed (recycled) to the dehydration column, and the remaining portion (19 parts) was recycled as a distillate liquid to the reaction system. The reflux ratio (amount refluxed/amount of the distillate) of the dehydration column was set at 0.3. As the result, 46 parts of product acetic acid were obtained as the bottom fraction from the column bottom of the dehydration column. In the product acetic acid, the crotonaldehyde content was 0.99 ppm, the 2-ethyl crotonaldehyde content was 0.03 ppm, and the butyl acetate content was 0.76 ppm. The permanganate time (chameleon time) of the product acetic acid was measured as 50 minutes. The results are shown in Table 1.

Example 1

The same experiment as in Comparative Example 1 was conducted except that 20 parts out of 41 parts of the organic phase [Composition: 0.3% of alkanes, 1300 ppm of acetaldehyde, 12.5% of methyl acetate, 0.7% of water, 1.9% of acetic acid, 1.5 ppm of crotonaldehyde, 0.1 ppm of 2-ethyl crotonaldehyde, 0.3 ppm of butyl acetate, and methyl iodide as a balance (however, a very small amount of impurities were contained)] recycled directly to the reaction vessel in Comparative Example 1 were fed to the crotonaldehyde removal column [packed column; theoretical number of plates: 10, feeding position: the fifth theoretical plate from the bottom, column top pressure of 280 kPa (absolute pressure), and column top temperature of 52° C.] (another 21 parts of the organic phase was directly recycled to the reaction vessel), to distill out 19.48 parts at a reflux ratio of 0.01 [Distillate composition: 1305 ppm of acetaldehyde, 12.5% of methyl acetate, 0.7% of water, 0.1% of acetic acid, 1.4 ppm of crotonaldehyde, 0.05 ppm of 2-ethyl crotonaldehyde, 0.2 ppm of butyl acetate, and methyl iodide as a balance (however, a very small amount of impurities were contained)], which was circulated to the decanter, and 0.52 parts of a bottom fraction [Bottom composition: 2.1% of methyl acetate, 1.5% of water, 5.5% of methyl iodide, 6.4 ppm of crotonaldehyde, 13.3 ppm of 2-ethyl crotonaldehyde, 6.9 ppm of butyl acetate, 1.2% of alkanes, and acetic acid as a balance (however, a very small amount of impurities were contained)] were withdrawn from the column bottom. With this change, the compositions of the respective process solutions were changed. As the result, in the product acetic acid obtained as the bottom fraction from the column bottom of the dehydration column the crotonaldehyde content was 0.95 ppm, the 2-ethyl crotonaldehyde content was 0.03 ppm, and the butyl acetate content was 0.71 ppm. The permanganate time (chameleon time) of the product acetic acid was measured as 70 minutes. The results are shown in Table 1.

Example 2

The same experiment as in Example 1 was conducted except that the reflux ratio of the lower boiling point component removal column was changed to 15, and the reflux ratio of the dehydration column was changed to 10. With this change, the compositions of the respective process solutions were changed. As the result, in the product acetic acid obtained from the column bottom of the dehydration column the crotonaldehyde content was 0.24 ppm, the 2-ethyl crotonaldehyde content was 0.19 ppm, and the butyl acetate content was 2.1 ppm. The permanganate time (chameleon time) of the product acetic acid was measured as 200 minutes. The results are shown in Table 1.

Example 3

The same experiment as in Example 2 was conducted except that the reflux ratio of the crotonaldehyde removal column was changed to 0.1. With this change, the compositions of the respective process solutions were changed. Further, the amount of the distillate liquid and the amount of the bottom fraction the crotonaldehyde removal column were changed to 19.52 parts and 0.48 parts, respectively. The above was caused because water distilled out to the column top was separated better, and was eventually separated into the bottom fraction. As the result, in the product acetic acid obtained from the column bottom of the dehydration column the crotonaldehyde content was 0.23 ppm, the 2-ethyl crotonaldehyde content was 0.18 ppm, and the butyl acetate content was 2.0 ppm. The permanganate time (chameleon time) of the product acetic acid was measured as 220 minutes. The results are shown in Table 1.

Example 4

The same experiment as in Example 2 was conducted except that the reflux ratio of the crotonaldehyde removal column was changed to 1. With this change, the compositions of the respective process solutions were changed. Further, the amount of the distillate liquid and the amount of the bottom fraction of the crotonaldehyde removal column were changed to 19.56 parts and 0.44 parts, respectively. The above was caused because water distilled out to the column top was separated far better, and was eventually separated into the bottom fraction. As the result, in the product acetic acid obtained from the column bottom of the dehydration column the crotonaldehyde content was 0.20 ppm, the 2-ethyl crotonaldehyde content was 0.18 ppm, and the butyl acetate content was 1.8 ppm. The permanganate time (chameleon time) of the product acetic acid was measured as 280 minutes. The results are shown in Table 1.

Example 5

The same experiment as in Example 2 was conducted except that the reflux ratio of the crotonaldehyde removal column was changed to 10. With this change, the compositions of the respective process solutions were changed. Further, the amount of the distillate liquid and the amount of the bottom fraction of the crotonaldehyde removal column were changed to 19.6 parts and 0.4 parts, respectively. The above was caused because water distilled out to the column top was separated far better, and was eventually separated into the bottom fraction. As the result, in the product acetic acid obtained from the column bottom of the dehydration column the crotonaldehyde content was 0.18 ppm, the 2-ethyl crotonaldehyde content was 0.16 ppm, and the butyl acetate content was 1.8 ppm. The permanganate time (chameleon time) of the product acetic acid was measured as 360 minutes. The results are shown in Table 1.

Example 6

The same experiment as in Example 2 was conducted except that the reflux ratio of the dehydration column was changed to 20, and the reflux ratio of the crotonaldehyde removal column was changed to 50. With this change, the compositions of the respective process solutions were changed. Further, the amount of the distillate liquid of the crotonaldehyde removal column was 19.6 parts, and the distillate composition was: 1298 ppm of acetaldehyde, 12.5% of methyl acetate, 0.7% of water, 0.01% of acetic acid, 0.1 ppm of crotonaldehyde, 0.00 ppm of 2-ethyl crotonaldehyde, 0.00 ppm of butyl acetate, and methyl iodide as a balance (however, a very small amount of impurities were contained). The amount of the bottom fraction of the crotonaldehyde removal column was 0.4 parts, and the bottom fraction composition was: 0.3% of methyl acetate, 0.1% of water, 0.05% of methyl iodide, 120 ppm of crotonaldehyde, 13.5 ppm of 2-ethyl crotonaldehyde, 6.9 ppm of butyl acetate, 1.2% of alkanes, and acetic acid as a balance (however, a very small amount of impurities were contained). As the result, in the product acetic acid obtained from the column bottom of the dehydration column the crotonaldehyde content was 0.16 ppm, the 2-ethyl crotonaldehyde content was 0.14 ppm, and the butyl acetate content was 1.6 ppm. The permanganate time (chameleon time) of the product acetic acid was measured and it was more than 420 minutes. The results are shown in Table 1.

In Table 1, CR stands for crotonaldehyde, 2ECR for 2-ethyl crotonaldehyde, and BA for methyl acetate. In Table 1, Numerical values in the columns with respect to each component represent concentrations. Distillate liquid [CR]/ charging mixture [CR] represents a ratio of the crotonaldehyde concentration (ppm by mass) in a distillate liquid to the crotonaldehyde concentration (ppm by mass) in a charging mixture (former/latter). Bottom fraction [CR]/charging mixture [CR] represents a ratio of the crotonaldehyde concentration (ppm by mass) in a bottom fraction to the crotonaldehyde concentration (ppm by mass) in a charging mixture (former/latter).

can still contribute to separation of crotonaldehyde, because almost all the charging mixture is distilled out by the present distillation, so that the rate of the distillate is very high and at nearly the same level as the amount of the charging mixture. The methyl iodide concentration in the bottom fraction in Example 6 is decreased to the lowest limit, so that the amount discharged of useful methyl iodide is suppressed.

TABLE 1

| | | Comparative Example | Examples | | | | | |
|---|---|---|---|---|---|---|---|---|
| | | 1 | 1 | 2 | 3 | 4 | 5 | 6 |
| Reflux ratio of lower boiling point component removal column | | 2 | 2 | 15 | 15 | 15 | 15 | 15 |
| Reflux ratio of dehydration column | | 0.3 | 0.3 | 10 | 10 | 10 | 10 | 20 |
| Reflux ratio of crotonaldehyde removal column | | — | 0.01 | 0.01 | 0.1 | 1 | 10 | 50 |
| Reaction mixture liquid | CR (ppm) | 1.3 | 1.1 | 1.1 | 1.1 | 1.0 | 0.9 | 0.9 |
| | 2ECR (ppm) | 1.5 | 1.4 | 1.4 | 1.4 | 1.4 | 1.3 | 1.2 |
| | BA (ppm) | 4.5 | 4.4 | 9.0 | 8.7 | 8.2 | 8.0 | 7.8 |
| Feed to lower boiling point component removal column | CR (ppm) | 1.4 | 1.3 | 1.3 | 1.3 | 1.2 | 1.1 | 1.0 |
| | 2ECR (ppm) | 0.22 | 0.24 | 0.34 | 0.33 | 0.32 | 0.32 | 0.30 |
| | BA (ppm) | 0.6 | 0.7 | 1.2 | 1.4 | 1.3 | 1.1 | 1.0 |
| Side cut liquid of lower boiling point component removal column | CR (ppm) | 1.1 | 1.0 | 0.4 | 0.4 | 0.3 | 0.2 | 0.2 |
| | 2ECR (ppm) | 0.2 | 0.2 | 0.4 | 0.4 | 0.4 | 0.3 | 0.2 |
| | BA (ppm) | 0.6 | 0.6 | 1.6 | 1.4 | 1.3 | 1.3 | 1.2 |
| Crotonaldehyde removal column | Charging mixture CR (ppm) | — | 1.5 | 2.6 | 2.6 | 2.6 | 2.5 | 2.5 |
| | Distillate liquid CR (ppm) | — | 1.4 | 2.5 | 2.3 | 1.0 | 0.3 | 0.1 |
| | Bottom fraction CR (ppm) | — | 6.4 | 7.5 | 17.3 | 81 | 110 | 120 |
| | Distillate liquid [CR]/ Charging mixture [CR] | — | 0.93 | 0.96 | 0.88 | 0.38 | 0.12 | 0.04 |
| | Bottom fraction [CR]/ Charging mixture [CR] | — | 4.3 | 2.9 | 6.7 | 31 | 44 | 48 |
| Bottom fraction of dehydration column (Product) | CR (ppm) | 0.99 | 0.95 | 0.24 | 0.23 | 0.20 | 0.18 | 0.16 |
| | 2ECR (ppm) | 0.03 | 0.03 | 0.19 | 0.18 | 0.18 | 0.16 | 0.14 |
| | BA (ppm) | 0.76 | 0.71 | 2.1 | 2.0 | 1.8 | 1.8 | 1.6 |
| Product chameleon time (minutes) | | 50 | 70 | 200 | 220 | 280 | 360 | 420< |

[Discussion on Results]

From the comparison of Comparative Example 1 and Example 1, It is evident that by setting the reflux ratio of a lower boiling point component removal column at a value of not less than a specific value, and operating the crotonaldehyde removal column under specific conditions, the crotonaldehyde concentration in product acetic acid is lowered, and the chameleon time is also improved.

From the comparison of Example 1 and Example 2, It is evident that even under the same operating conditions of the crotonaldehyde removal column, if the reflux ratios of a lower boiling point component removal column, and a dehydration column are increased, the product chameleon time is improved remarkably. Referring to Examples 2 to 6, even under the same reflux ratio conditions with respect to a lower boiling point component removal column, if the reflux ratio of the crotonaldehyde removal column is increased such that crotonaldehyde is more concentrated at the column bottom of the crotonaldehyde removal column, the amount of crotonaldehyde discarded is increased, and therefore the chameleon time of product acetic acid is improved.

Although the reflux ratio of the crotonaldehyde removal column in Examples 1, and 2 is 0.01, which is extremely low compared with ordinary distillation, such a low reflux rate From the above, it is evident that if the reflux ratios of the lower boiling point component removal column and/or the dehydration column are increased so as to concentrate crotonaldehyde at the column top, and to recycle the same to a reaction vessel; in the reaction vessel crotonaldehyde is transformed to 2-ethyl crotonaldehyde or butyl acetate (crotonaldehyde+acetaldehyde→2-ethyl crotonaldehyde, crotonaldehyde+hydrogen→butyl alcohol, butyl alcohol+acetic acid→butyl acetate); and crotonaldehyde is removed efficiently by increasing the reflux ratio of the lower boiling point component removal column to concentrate crotonaldehyde at the column top, and conducting a distillation operation on the column top fraction (for example, organic phase), owing to the synergistic effect thereof, unexpected quality improvement can be attained.

In conclusion, the composition of the present invention and its variations are appended below.

[1] A method for producing acetic acid comprising:
a carbonylation reaction step of reacting methanol with carbon monoxide in the presence of a catalyst system containing a metal catalyst and methyl iodide, as well as acetic acid, methyl acetate, and water in a reaction vessel to produce acetic acid;
an evaporation step of separating a reaction mixture obtained in the carbonylation reaction step into a vapor stream and a residual liquid stream in an evaporator;

a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase;

a first overhead stream recycle step of recycling at least a portion of the aqueous phase and/or organic phase to a reaction vessel; and a crotonaldehyde removal step of separating and removing crotonaldehyde by treating at least another portion of the aqueous phase and/or organic phase by a distillation column;

wherein with respect to a reflux ratio of the first distillation column, when only the aqueous phase is refluxed to the first distillation column, a reflux ratio of the aqueous phase is not less than 2, when only the organic phase is refluxed, a reflux ratio of the organic phase is not less than 1, and when both the aqueous phase and the organic phase are refluxed, a total reflux ratio of the aqueous phase and the organic phase is not less than 1.5; and in the crotonaldehyde removal step the distillation column is operated such that at least one of the following conditions (i) to (iii) is satisfied:

(i) the reflux ratio of the distillation column is not less than 0.01;

(ii) a ratio of the crotonaldehyde concentration (ppm by mass) in a distillate liquid of the distillation column to the crotonaldehyde concentration (ppm by mass) in a charging mixture (former/latter) is less than 1; and (iii) a ratio of the crotonaldehyde concentration (ppm by mass) in a bottom fraction of the distillation column to the crotonaldehyde concentration (ppm by mass) in the charging mixture (former/latter) is more than 1.

[2] The method for producing acetic acid according to [1], further comprising a dehydration step of separating the first acetic acid stream by a second distillation column into a second overhead stream rich in water and a second acetic acid stream more enriched with acetic acid than the first acetic acid stream.

[3] The method for producing acetic acid according to [2], wherein a reflux ratio of the second distillation column is not less than 0.3 (preferably not less than 1.0, more preferably not less than 5.0, further preferably not less than 10, and particularly preferably not less than 12).

[4] The method for producing acetic acid according to [2] or [3], wherein in the second acetic acid stream a crotonaldehyde concentration is not more than 0.98 ppm by mass (preferably not more than 0.80 ppm by mass, more preferably not more than 0.50 ppm by mass, and further preferably not more than 0.30 ppm by mass), and/or a 2-ethyl crotonaldehyde concentration is not more than 1.0 ppm by mass (preferably not more than 0.50 ppm by mass, more preferably not more than 0.30 ppm by mass, and further preferably not more than 0.20 ppm by mass), and/or a butyl acetate concentration is not more than 15 ppm by mass (preferably not more than 10 ppm by mass, more preferably not more than 8 ppm by mass, further preferably not more than 5 ppm by mass, and particularly preferably not more than 3 ppm by mass).

[5] The method for producing acetic acid according to any one of [2] to [4], wherein a potassium permanganate test value of the second acetic acid stream is more than 50 minutes (preferably not less than 60 minutes, more preferably not less than 100 minutes, further preferably not less than 120 minutes, particularly preferably not less than 180 minutes, especially preferably not less than 240 minutes, and among others not less than 360 minutes).

[6] The method for producing acetic acid according to any one of [2] to [5], wherein an upper limit of the reflux ratio of the second distillation column is 3000 (preferably 1000, more preferably 200, and further preferably 100).

[7] The method for producing acetic acid according to any one of [1] to [6], wherein the catalyst system further contains an ionic iodide.

[8] The method for producing acetic acid according to any one of [1] to [7], further comprising an acetaldehyde separation and removal step of separating and removing acetaldehyde by distilling at least a portion of the aqueous phase and/or the organic phase obtained by condensing the first overhead stream.

[9] The method for producing acetic acid according to [8], wherein at least a portion of a residual liquid after separating and removing acetaldehyde from at least a portion of the aqueous phase and/or the organic phase is recycled to the reaction vessel.

[10] The method for producing acetic acid according to any one of [1] to [9], wherein in the vapor stream fed to the first distillation column a crotonaldehyde concentration is 0 to 5.0 ppm by mass (preferably 0.01 to 4.0 ppm by mass, more preferably 0.1 to 3.0 ppm by mass, and further preferably 0.2 to 2.0 ppm by mass), and/or a 2-ethyl crotonaldehyde concentration is 0 to 3.0 ppm by mass (preferably 0.01 to 2.5 ppm by mass, more preferably 0.02 to 2.0 ppm by mass, and further preferably 0.03 to 0.8 ppm by mass), and/or a butyl acetate concentration is 0.1 to 13.0 ppm by mass (preferably 0.2 to 12.0 ppm by mass, and more preferably 0.3 to 9.0 ppm by mass).

[11] The method for producing acetic acid according to any one of [1] to [10], wherein in the first acetic acid stream a crotonaldehyde concentration is not more than 1.3 ppm by mass (preferably not more than 1.0 ppm by mass, more preferably not more than 0.85 ppm by mass, further preferably not more than 0.5 ppm by mass, and particularly preferably not more than 0.25 ppm by mass), and/or a 2-ethyl crotonaldehyde concentration is not more than 1.0 ppm by mass (preferably not more than 0.50 ppm by mass), and/or a butyl acetate concentration is not more than 15 ppm by mass (preferably not more than 10 ppm by mass, more preferably not more than 8 ppm by mass, further preferably not more than 5 ppm by mass, and particularly preferably not more than 3 ppm by mass).

[12] The method for producing acetic acid according to any one of [1] to [11], wherein a crotonaldehyde concentration in a distillation column charging mixture in the crotonaldehyde removal step is 0.01 to 50 ppm by mass (preferably 0.1 to 50 ppm by mass, more preferably 0.3 to 30 ppm by mass, further preferably 0.5 to 10 ppm by mass, particularly preferably 0.8 to 7.0 ppm by mass, especially 1.0 to 5.0 ppm by mass).

[13] The method for producing acetic acid according to any one of [1] to [12], wherein in the crotonaldehyde removal step the distillation column is operated such that all the conditions (i) to (iii) are satisfied.

[14] The method for producing acetic acid according to any one of [1] to [13], wherein distillation is performed by a batch process in the crotonaldehyde removal step.

[15] The method for producing acetic acid according to any one of [1] to [14], wherein a throughput of the distillation column in the crotonaldehyde removal step is 0.0001 to 50 parts by mass (preferably 0.001 to 30 parts by mass, more preferably 0.01 to 10 parts by mass, and further preferably 0.1 to 5 parts by mass) with respect to an amount of the vapor stream fed to the first distillation column of 100 parts by mass.

[16] The method for producing acetic acid according to any one of [1] to [15], wherein a column top condensate of the distillation column in the crotonaldehyde removal step is recycled to the aqueous phase and/or the organic phase and/or the reaction vessel.

[17] The method for producing acetic acid according to any one of [1] to [16], wherein with respect to the reflux ratio of the first distillation column, when only the aqueous phase is refluxed to the first distillation column, the reflux ratio of the aqueous phase is not less than 3 (preferably not less than 5, more preferably not less than 8, and further preferably not less than 12).

[18] The method for producing acetic acid according to any one of [1] to [17], wherein with respect to the reflux ratio of the first distillation column, when only the organic phase is refluxed to the first distillation column, the reflux ratio of the aqueous phase is not less than 1.5 (preferably not less than 2, more preferably not less than 4, and further preferably not less than 5).

[19] The method for producing acetic acid according to any one of [1] to [18], wherein with respect to the reflux ratio of the first distillation column, when both the aqueous phase and the organic phase are refluxed to the first distillation column, the total reflux ratio of the aqueous phase and the organic phase is not less than 2.3 (preferably not less than 3.5, more preferably not less than 6, and further preferably not less than 8.5).

[20] The method for producing acetic acid according to any one of [1] to [19], wherein an upper limit of the reflux ratio of the first distillation column is 3000 (preferably 1000, more preferably 100, and further preferably 30).

[21] The method for producing acetic acid according to any one of [1] to [20], wherein in (i) above, the reflux ratio of the distillation column is not less than 0.05 (preferably not less than 0.5, more preferably not less than 5, further preferably not less than 20, and particularly preferably not less than 30).

[22] The method for producing acetic acid according to any one of [1] to [21], wherein in (i) above, an upper limit of the reflux ratio of the distillation column is 1000.

[23] The method for producing acetic acid according to any one of [1] to [22], wherein in (ii) above, the ratio of the crotonaldehyde concentration (ppm by mass) in the distillate liquid of the distillation column to the crotonaldehyde concentration (ppm by mass) in the charging mixture (former/latter) is not more than 0.95 (preferably not more than 0.80, more preferably not more than 0.70, further preferably not more than 0.60, particularly preferably not more than 0.50, especially preferably not more than 0.30, and among others not more than 0.20).

[24] The method for producing acetic acid according to any one of [1] to [23], wherein in (iii) above, the ratio of the crotonaldehyde concentration (ppm by mass) in the bottom fraction of the distillation column to the crotonaldehyde concentration (ppm by mass) in the charging mixture (former/latter) is not less than 1.2 (preferably not less than 1.5, more preferably not less than 2.0, further preferably not less than 3.0, particularly preferably not less than 4.0, especially preferably not less than 5.0, still further preferably not less than 10, and among others not less than 20).

[25] The method for producing acetic acid according to any one of [1] to [24], wherein crotonaldehyde is concentrated at the column bottom of the distillation column in the crotonaldehyde removal step, and discharged out of the system as the bottom fraction together with acetic acid.

[26] The method for producing acetic acid according to any one of [1] to [25], wherein an acetaldehyde concentration in a reaction mixture liquid in the reaction vessel is not more than 500 ppm by mass (preferably not more than 450 ppm by mass, more preferably not more than 400 ppm by mass, further preferably not more than 350 ppm by mass, particularly preferably not more than 300 ppm by mass, and especially not more than 250 ppm by mass).

[27] The method for producing acetic acid according to any one of [1] to [26], wherein a crotonaldehyde concentration in a reaction mixture liquid in the reaction vessel is not more than 5 ppm by mass (preferably not more than 3 ppm by mass, and more preferably not more than 2 ppm by mass).

[28] The method for producing acetic acid according to any one of [1] to [27], wherein a 2-ethyl crotonaldehyde concentration in a reaction mixture liquid in the reaction vessel is not more than 5 ppm by mass (preferably not more than 3 ppm by mass, and more preferably not more than 2 ppm by mass).

[29] The method for producing acetic acid according to any one of [1] to [28], wherein a butyl acetate concentration in a reaction mixture liquid in the reaction vessel is 0.1 to 15 ppm by mass (preferably 1 to 12 ppm by mass, and more preferably 2 to 9 ppm by mass).

[30] The method for producing acetic acid according to any one of [1] to [29], wherein a hydrogen partial pressure in the reaction vessel is not less than 0.01 MPa (absolute pressure) (preferably not less than 0.015 MPa (absolute pressure), more preferably not less than 0.02 MPa (absolute pressure), further preferably not less than 0.04 MPa (absolute pressure), particularly preferably not less than 0.06 MPa (absolute pressure), and especially not less than 0.07 MPa (absolute pressure)).

[31] The method for producing acetic acid according to any one of [1] to [30], wherein an upper limit of a hydrogen partial pressure in the reaction vessel is 0.5 MPa (absolute pressure) (preferably 0.2 MPa (absolute pressure)).

[32] The method for producing acetic acid according to any one of [1] to [31], wherein a feeding position of a feeding liquid to the distillation column in the crotonaldehyde removal step in a case where distillation is conducted continuously is a position 20% to 80% (²⁄₁₀ to ⁸⁄₁₀) downward from the top in a height direction of the distillation column.

[33] The method for producing acetic acid according to any one of [1] to [32], wherein in the crotonaldehyde removal step at least a portion of a condensate of a column top vapor of the distillation column is refluxed to the distillation column, and at least another portion of the condensate is withdrawn as the distillate liquid and recycled to the aqueous phase and/or the organic phase and/or the reaction vessel.

[34] The method for producing acetic acid according to any one of [1] to [33], wherein a bottom fraction containing crotonaldehyde is withdrawn from the column bottom of the distillation column in the crotonaldehyde removal step.

[35] The method for producing acetic acid according to any one of [1] to [34], wherein with respect to the reflux ratio of the first distillation column the reflux ratio of the aqueous phase is not less than 2.

INDUSTRIAL APPLICABILITY

A method for producing acetic acid according to the present invention can be used as an industrial method for producing acetic acid by a carbonylation process of a methanol method (acetic acid production process of a methanol method).

REFERENCE SIGNS LIST

1: reaction vessel
2: evaporator 3, 5, 6, and 10: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray

The invention claimed is:

1. A method for producing acetic acid, comprising:
carbonylating methanol with carbon monoxide in the presence of a catalyst system containing a metal catalyst and methyl iodide, as well as acetic acid, methyl acetate, and water in a reaction vessel to produce acetic acid;
evaporating a reaction mixture obtained by the carbonylation to separate into a vapor stream and a residual liquid stream in an evaporator;
removing a lower boiling point component to separate the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase;
dehydrating the first acetic acid stream by a second distillation column to separate into a second overhead stream rich in water and a second acetic acid stream more enriched with acetic acid than the first acetic acid stream;
recycling at least a portion of the aqueous phase and/or organic phase in the first overhead stream to a reaction vessel; and
separating and removing crotonaldehyde by treating at least another portion of the aqueous phase and/or organic phase by a distillation column;
wherein a potassium permanganate test value of the second acetic acid stream is more than 50 minutes; and
wherein with respect to a reflux ratio of the first distillation column, when only the aqueous phase is refluxed to the first distillation column, a reflux ratio of the aqueous phase is not less than 2, when only the organic phase is refluxed, a reflux ratio of the organic phase is not less than 1, and when both the aqueous phase and the organic phase are refluxed, a total reflux ratio of the aqueous phase and the organic phase is not less than 1.5; and when removing the crotonaldehyde, the distillation column is operated such that all of the following conditions (i) to (iii) are satisfied:
(i) the reflux ratio of the distillation column is not less than 0.01;
(ii) a ratio of a crotonaldehyde concentration in ppm by mass in a distillate liquid of the distillation column to a crotonaldehyde concentration in ppm by mass in a charging mixture, former/latter, is less than 1; and
(iii) a ratio of a crotonaldehyde concentration in ppm by mass in a bottom fraction of the distillation column to the crotonaldehyde concentration in ppm by mass in the charging mixture, former/latter, is more than 1.

2. The method for producing acetic acid according to claim 1, wherein a reflux ratio of the second distillation column is not less than 0.3.

3. The method for producing acetic acid according to claim 1, wherein in the second acetic acid stream a crotonaldehyde concentration is not more than 0.98 ppm by mass, and/or a 2-ethyl crotonaldehyde concentration is not more than 1.0 ppm by mass, and/or a butyl acetate concentration is not more than 15 ppm by mass.

4. The method for producing acetic acid according to claim 1, wherein the catalyst system further contains an ionic iodide.

5. The method for producing acetic acid according to claim 1, further comprising separating and removing acetaldehyde by distilling at least a portion of the aqueous phase and/or the organic phase obtained by condensing the first overhead stream.

6. The method for producing acetic acid according to claim 5, wherein at least a portion of a residual liquid after separating and removing acetaldehyde from at least a portion of the aqueous phase and/or the organic phase is recycled to the reaction vessel.

7. The method for producing acetic acid according to claim 1, wherein in the vapor stream fed to the first distillation column a crotonaldehyde concentration is 0 to 5.0 ppm by mass, and/or a 2-ethyl crotonaldehyde concentration is 0 to 3.0 ppm by mass, and/or a butyl acetate concentration is 0.1 to 13.0 ppm by mass.

8. The method for producing acetic acid according to claim 1, wherein in the first acetic acid stream a crotonaldehyde concentration is not more than 1.3 ppm by mass, and/or a 2-ethyl crotonaldehyde concentration is not more than 1.0 ppm by mass, and/or a butyl acetate concentration is not more than 15 ppm by mass.

9. The method for producing acetic acid according to claim 1, wherein a crotonaldehyde concentration in a distillation column charging mixture when removing the crotonaldehyde is 0.01 to 50 ppm by mass.

10. The method for producing acetic acid according to claim 1, wherein distillation is performed by a batch process when removing the crotonaldehyde.

11. The method for producing acetic acid according to claim 1, wherein a throughput of the distillation column for removing the crotonaldehyde is 0.0001 to 50 parts by mass with respect to an amount of the vapor stream fed to the first distillation column of 100 parts by mass.

12. The method for producing acetic acid according to claim 1, wherein in the second acetic acid stream a crotonaldehyde concentration is not more than 0.80 ppm by mass, and/or a 2-ethyl crotonaldehyde concentration is not more than 0.50 ppm by mass, and/or a butyl acetate concentration is not more than 10 ppm by mass.

13. The method for producing acetic acid according to claim 1, wherein in the vapor stream fed to the first distillation column a crotonaldehyde concentration is 0.01 to 4.0 ppm by mass, and/or a 2-ethyl crotonaldehyde concentration is 0.01 to 2.5 ppm by mass, and/or a butyl acetate concentration is 0.2 to 12.0 ppm by mass.

14. The method for producing acetic acid according to claim 1, wherein in the first acetic acid stream a crotonaldehyde concentration is not more than 1.0 ppm by mass, and/or a 2-ethyl crotonaldehyde concentration is not more than 0.50 ppm by mass, and/or a butyl acetate concentration is not more than 10 ppm by mass.

15. The method for producing acetic acid according to claim 1, wherein a crotonaldehyde concentration in a distillation column charging mixture when removing the crotonaldehyde is 0.3 to 30 ppm by mass.

16. The method for producing acetic acid according to claim 1, wherein a throughput of the distillation column for removing the crotonaldehyde is 0.001 to 30 parts by mass.

17. The method for producing acetic acid according to claim 1, wherein with respect to a reflux ratio of the first distillation column, when only the aqueous phase is refluxed to the first distillation column, a reflux ratio of the aqueous phase is not less than 3, when only the organic phase is refluxed, a reflux ratio of the organic phase is not less than 1.5, and when both the aqueous phase and the organic phase are refluxed, a total reflux ratio of the aqueous phase and the organic phase is not less than 2.3.

18. The method for producing acetic acid according to claim 1, wherein in (ii) above, the ratio of the crotonaldehyde concentration in ppm by mass in the distillate liquid of the distillation column to the crotonaldehyde concentration in ppm by mass in the charging mixture, former/latter, is not more than 0.95, and in (iii) above, the ratio of the crotonaldehyde concentration in ppm by mass in the bottom fraction of the distillation column to the crotonaldehyde concentration in ppm by mass in the charging mixture, former/latter, is not less than 1.2.

19. The method for producing acetic acid according to claim 1, wherein an acetaldehyde concentration in a reaction mixture liquid in the reaction vessel is not more than 500 ppm by mass, and/or a crotonaldehyde concentration in a reaction mixture liquid in the reaction vessel is not more than 5 ppm by mass, and/or a 2-ethyl crotonaldehyde concentration in a reaction mixture liquid in the reaction vessel is not more than 5 ppm by mass.

20. The method for producing acetic acid according to claim 1, wherein a feeding position of a feeding liquid to the distillation column for removing the crotonaldehyde in a case where distillation is conducted continuously is a position 20% to 80% downward from the top in a height direction of the distillation column.

\* \* \* \* \*